US011860123B2

(12) United States Patent
Leburton et al.

(10) Patent No.: US 11,860,123 B2
(45) Date of Patent: Jan. 2, 2024

(54) CLASSIFICATION OF EPIGENETIC BIOMARKERS AND/OR DNA CONFORMATIONAL SUPERSTRUCTURES VIA USE OF ATOMICALLY THIN NANOPORES

(71) Applicant: THE BOARD OF TRUSTEES OF THE UNIVERSITY OF ILLINOIS, Urbana, IL (US)

(72) Inventors: Jean-Pierre Leburton, Urbana, IL (US); Lav Raj Varshney, Champaign, IL (US); Aditya Sarathy, Santa Clara, CA (US); Nagendra B. Athreya, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 702 days.

(21) Appl. No.: 16/850,575

(22) Filed: Apr. 16, 2020

(65) Prior Publication Data
US 2020/0333290 A1 Oct. 22, 2020

Related U.S. Application Data

(60) Provisional application No. 62/834,842, filed on Apr. 16, 2019.

(51) Int. Cl.
*G01N 27/447* (2006.01)
*C12Q 1/6874* (2018.01)
*G01N 33/487* (2006.01)
*B82Y 5/00* (2011.01)

(52) U.S. Cl.
CPC ..... *G01N 27/44791* (2013.01); *C12Q 1/6874* (2013.01); *G01N 33/48721* (2013.01); *B82Y 5/00* (2013.01); *C12Q 2565/631* (2013.01)

(58) Field of Classification Search
CPC ....... G01N 27/44791; G01N 33/48721; C12Q 1/6874; C12Q 2565/631; C12Q 1/6827; C12Q 1/6869; C12Q 2522/101; C12Q 2537/164; B82Y 5/00
See application file for complete search history.

(56) References Cited

U.S. PATENT DOCUMENTS

| | | | |
|---|---|---|---|
| 8,192,600 | B2 | 6/2012 | Leburton et al. |
| 8,394,584 | B2 | 3/2013 | Timp et al. |
| 8,702,929 | B2 | 4/2014 | Leburton et al. |
| 9,957,560 | B2 | 5/2018 | Brown et al. |
| 2013/0071837 | A1 | 3/2013 | Winters-hilt et al. |
| 2014/0174927 | A1 | 6/2014 | Bashir et al. |
| 2015/0259724 | A1 | 9/2015 | Guan et al. |
| 2016/0054260 | A1 | 2/2016 | Leburton |
| 2017/0022546 | A1 | 1/2017 | Bashir |
| 2018/0088104 | A1* | 3/2018 | Aksimentiev .... G01N 33/48721 |

FOREIGN PATENT DOCUMENTS

| | | | |
|---|---|---|---|
| WO | 2010080617 A2 | 7/2010 | |
| WO | WO-2014071250 A1 * | 5/2014 | ........... C12Q 1/6827 |

OTHER PUBLICATIONS

Madrid, Jul. 23-27, 2018: ICSNN: International Conference on Superlattices, Nanostructures and Nanodevices; https://icmab.es/icsnn; pp. 1-4.
Laird, Peter W., Early detection: The power and the promise of DNA methylation markers, Nature Reviews Cancer 3, 253-266, Apr. 2003., 15 pages.
Leburton, Jean Pierre, Electronic Bio-Sensing in 2D Nanopore FET; seminar materials, earliest use dated May 9, 2018, pp. 1-29.
Sarathy, et al., "Classification of Epigenetic Biomarkers with Atomically Thin Nanopores", Sep. 18, 2018, 8 pages.
Sarathy, et al., "Classification of Epigenetic Biomarkers with Atomically-Thin Nanopores: Supporting Information", Sep. 18, 2018, 7 pages.
Sarathy, Aditya et al., "Electronic conductance model in constricted MoS2 with Nanopores" Appl. Phys. Letters. 108, 053701, pp. 1-5 (2016).
Sarathy, Aditya, Decoding Biology with Physics and Chemistry; Seminar Materials, Undated, pp. 1-21.
Wallace, Emma V.B. et al., Identification of epigenetic DNA modifications with a protein nanopore , National Center for Biotechnology Information, https://www.ncbi.nlm.nih.gov/pmc/articles/PMC3147113 //; Chem Commun (Camb). Nov. 2, 20101; 7 pages.
Athreya, N. B. M. et al., Large Scale Parallel DNA Detection by Two-Dimensional Solid-State Multipore Systems; Apr. 17, 2018, 3, 1032-1039.
Bayley, H., Nanotechnology: holes with an edge. Nature, 2010, 164-165.
Du, Q. et al., Methyl-CpGbinding domain proteins: readers of the epigenome. Epigenomics, 2015, 1051-1073.

(Continued)

*Primary Examiner* — Narayan K Bhat
(74) *Attorney, Agent, or Firm* — Guntin & Gust, PLC; Matthew Tropper

(57) ABSTRACT

An apparatus comprising: a membrane with a first side, a second side, and a pore that extends through the membrane; a processing system including a processor; and a memory that stores executable instructions that, when executed by the processing system, facilitate performance of operations, the operations comprising: electronic sensing of an electrical characteristic associated with a translocation of a test DNA through the pore, resulting in a sensed electrical characteristic; comparing the sensed electrical characteristic with a plurality of reference electrical characteristics, wherein each of the plurality of reference electrical characteristics is associated with a respective one of a plurality of reference features, and wherein the comparing results in a comparison result; and determining, based upon the comparison result, with which of the plurality of reference features a feature of the test DNA corresponds. Additional embodiments are disclosed.

20 Claims, 14 Drawing Sheets

(56) References Cited

OTHER PUBLICATIONS

Ehrlich, M., DNA methylation in cancer: too much, but also too little. Oncogene, 2002, 5400-5413.
Essmann, U. et al., A smooth particle mesh Ewald method. J. Chem. Phys. 1995, 8577{8593.
Feller, S.E., Constant pressure molecular dynamics simulation: the Langevin piston method. J. Chem. Phys. 1995, 4613-4621.
Foloppe, N. et al., All-atom empirical force_eld for nucleic acids: I. Parameter optimization based on small molecule and condensed phase macromolecular target data. Journal of Computational Chemistry 2000, 86-104.
Furth, P.M et al., A design framework for low power analog filter banks. IEEE Trans. Circuits Syst. I, Fundam. Theory Appl. 1995, 966-971.
Garalde, D. R. et al., Highly parallel direct RNA sequencing on an array of nanopores. Nat. Methods, Jan. 15, 2018, 201-206.
Gilboa, T., Single-Molecule DNA Methylation Quantification Using Electro-optical Sensing in Solid-State Nanopores. ACS Nano, 2016, 8861-8870.
Girdhar, A. et al., Graphene quantum point contact transistor for DNA sensing. Proc. Natl. Acad. Sci. U. S. A. 2013, 16748-16753.
Gracheva, M.E. et al., Electrical signatures of single-stranded DNA with single base mutations in a nanopore capacitor. Nanotechnology 2006, 3160-3165.
Gracheva, M.E. et al., Electrolytic charge inversion at the liquid{solid interface in a nanopore in a doped semiconductor membrane. Nanotechnology 18, 2007, pp. 1-7; DOI:10.1088/0957-4484/18/14/145704.
Gracheva, M.E. , p-n Semiconductor Membrane for Electrically Tunable Ion Current Recti_cation and Filtering. Nano letters 2007, 1717-1722.
Gracheva, M.E. et al., Simulation of the electric response of DNA translocation through a semiconductor nanopore capacitor. Nanotechnology 2006, 622-633.
Heerema, S.J. et al., Graphene nanodevices for DNA sequencing. Nat. Nanotechnol. 2016, 127-136.
Heerema, S.J. et al., Probing DNA translocations with inplane current signals in a graphene nanoribbon with a nanopore. ACS Nano, Feb. 23, 2018, 2623-2633.
Ho, K.L. et al., MeCP2 Binding to DNA Depends upon Hydration at Methyl-CpG. Molecular Cell, 2008, 525-531.
Humphrey, W. et al., VMD: visual molecular dynamics. J. Mol. Graphics, 1996, 33-38.
Jain, M. et al., Nanopore sequencing and assembly of a human genome with ultralong reads. Nat. Biotechnol, Jan. 29, 2018, 338-345.
Jang, J.-S. et al., Methyl-CpG binding domain 1 gene polymorphisms and risk of primary lung cancer. Cancer Epidemiol. Prev. Biomarkers 2005, 2474-2480.
Jorgensen, W. L., Comparison of simple potential functions for simulating liquid water. J. Chem. Phys. 1983, 926-935.
Kilianski, A. et al., Bacterial and viral identification and differentiation by amplicon sequencing on the MinION nanopore sequencer. GigaScience, 2015, p. 1-8.
Laszlo, A.H. et al., Detection and mapping of 5-methylcytosine and 5-hydroxymethylcytosine with nanopore MspA. Proc. Natl. Acad. Sci.U. S. A., 2013, 18904-18909.
Lopez-Serra, L. et al., Proteins that bind methylated DNA and human cancer: reading the wrong words. Br. J. Cancer, 2008, 1881-1885.
Mackerell, A.D. et al., All-Atom Empirical Potential for Molecular Modeling and Dynamics Studies of Proteins. The Journal of Physical Chemistry B, 1998, 3586-3616.
North, D.O., An Analysis of the factors which determine signal/noise discrimination in pulsed-carrier systems. Proc. IEEE, 1963, 1016-1027.
Ohki, I. et al., Solution Structure of the Methyl-CpG Binding Domain of Human MBD1 in Complex with Methylated DNA. Cell 2001, 487{ 497.
Parkin, W.M. et al., Signal and Noise in FET-Nanopore Devices. ACS Sensors, Jan. 11, 2018, 313-319.
Parry, L. et al., The roles of the methyl-CpG binding proteins in cancer. Genes Cancer, 2011, 618-630.
Phillips, J.C. et al., Scalable molecular dynamics with NAMD. Journal of Computational Chemistry, 2005, 1781-1802.
Qiu, Hu et al., Intrinsic Stepwise Translocation of Stretched ssDNA in Graphene Nanopores, Nano Lett., 2015, 8322-8330.
Qiu, Hu et al., Detection and Mapping of DNA Methylation with 2D Material Nanopores, npj 2D Materials and Applications; www.nature.com/npj2dmaterials, manuscript, Apr. 11, 2017, pp. 1-22.
Qiu, Hu et al., Detection and Mapping of DNA Methylation with 2D Material Nanopores, npj 2D Materials and Applications; www.nature.com/npj2dmaterials, Apr. 11, 2017, pp. 1-8.
Raillon, C. et al., Fast and automatic processing of multi-level events in nanopore translocation experiments. Nanoscale, 2012, 4916-4924.
Saenger, W. et al., Structures of the Common Cyclodextrins and Their Larger Analogues—Beyond the Doughnut. Chemical Reviews 1998, 1787-1802.
Sarathy, A. et al., Graphene nanopores for electronic recognition of DNA methylation. J. Phys. Chem. B, Dec. 30, 2016, 3757-3763.
Sarathy, Aditya et al., Electronic Conductance Model in Constricted MoS2 with Nanopore, Applied Physics Letters 108, (2016), pp. 1-5.
Sathe, C, Computational investigation of DNA detection using graphene nanopores. ACS Nano, 2011, 5, 8842-8851.
Shim, J. et al., Nanopore-based assay for detection of methylation in doublestranded DNA fragments. ACS Nano, 2015, 290-300.
Simpson, J. T. et al., Detecting DNA cytosine methylation using nanopore sequencing. Nat. Methods, Feb. 20, 2017, 407-410.
Stewart, J.A., Atomistic simulations of nanoindentation on the basal plane of crystalline molybdenum disul_de (MoS2). Modelling and Simulation in Materials Science and Engineering, 2013, pp. 1-15.
Turin, G., An introduction to matched filters. IRE Trans. Inf. Theory 1960, IT-6, 311-329.
Van Dijk, M., 3D-DART: a DNA structure modelling server. Nucleic Acids Research, 2009, W235-W239.

* cited by examiner

Sensing an electrical characteristic associated with a translocation of a test DNA through a pore, wherein a feature of the test DNA comprises an epigenetic biomarker, the test DNA itself forming a conformational superstructure, or any combination thereof, and wherein the sensing results in a sensed electrical characteristic
702

Comparing the sensed electrical characteristic with a plurality of reference electrical characteristics, wherein each of the plurality of reference electrical characteristics is associated with a respective one of a plurality of reference features, and wherein the comparing results in a comparison result
704

Determining, based upon the comparison result, with which of the plurality of reference features the feature of the test DNA corresponds
706

CLASSIFICATION OF EPIGENETIC BIOMARKERS AND/OR DNA CONFORMATIONAL SUPERSTRUCTURES VIA USE OF ATOMICALLY THIN NANOPORES

CROSS REFERENCE TO RELATED APPLICATION(S)

This application claims the benefit of priority to U.S. Provisional Application No. 62/834,842, filed Apr. 16, 2019. All sections of the aforementioned application(s) and/or patent(s) are incorporated herein by reference in their entirety (including each Appendix thereof).

FIELD OF THE DISCLOSURE

The subject disclosure relates generally to classification of epigenetic biomarkers and/or to classification of DNA conformational superstructures. In one specific example, the subject disclosure relates to classification of epigenetic biomarkers via use of atomically thin nanopores. In another specific example, the subject disclosure relates to classification of DNA conformational superstructures via use of atomically thin nanopores.

BACKGROUND

The search for a low-cost, fast, and reliable method to access and decode the human genome and epigenome is a technological challenge in modern medicine (see References 1A, 2A) which certain conventional biochemical sequencing processes (see Reference 3A) may not be able to meet. One possible alternative uses a very thin membrane with a nanoscale pore (see Reference 4A) through which DNA molecules are threaded to identify not only the nucleotide sequence but also traits of DNA such as methylation (see References 5A, 6A). Indeed, methylation may be as crucial as the sequence itself for the diagnosis and identification of epigenetic diseases such as cancer (see References 7A, 8A) through its role in silencing key cancer-related genes. Certain conventional commercially available biological nanopore sequencers that have been used to sequence DNA (see Reference 9A) and RNA (see Reference 10A) would be unable to identify epigenetic markers attached to methylated sites owing to size discrepancy between the DNA-marker complex and the nanopore. Therefore, solid-state nanopores may be the only viable solution as a versatile and general sensor technology for detecting methylation patterns.

It is known that the utilization of 2D materials in solid-state nanopores offers the highest detection resolution. In this regard, Girdhar et al. proposed the utilization of solid-state multilayer nanopore membranes within multifunctional electronic devices to increase their detection sensitivity (see Reference 11A). Qiu et al. further demonstrated that methylated cytosines labeled by methyl-CpG binding domain proteins can be detected with solid-state nanopores composed of 2D materials such as graphene or molybdenum disulfide ($MoS_2$) (see References 12A, 13A). This detection was based on two simultaneous signals: ionic current variations through the pore and electronic current changes along the 2D membrane. The two signals together yield higher protein identification and classification accuracy than a single signal alone. Whereas the ionic currents provide information regarding the size of the translocating biomarker via the current blockade and dwell time, the electronic sheet current variations are specifically dependent on the charge distribution within each biomarker, thereby providing unique signatures for each marker. It was also shown that the electronic sheet current detection of these labeled proteins offers a higher resolution in measurement as compared with ionic current-based detection (see Reference 14A). Indeed, the resolution in the detection of these labeled sites via electronic sheet current has no intrinsic limitation asides from the sizes of the labeled proteins. Aside from recent works (see References 14A, 15A) little attention has been paid to explore the utility of solid-state nanopores to identify epigenetic biomarkers along a double-stranded DNA that are indicative of intricate mechanisms of gene regulation (see Reference 16A). Also, efforts to detect, identify, and map DNA methylation patterns using solid-state nanopores have been unsuccessful because of the significant noise introduced in the measured signal due to the conformational stochastic fluctuations of DNA inside the pore.

BRIEF DESCRIPTION OF THE DRAWINGS

Reference will now be made to the accompanying drawings, which are not necessarily drawn to scale, and wherein:

FIG. 7 depicts an illustrative method according to an embodiment.

DETAILED DESCRIPTION

Figure 1A:
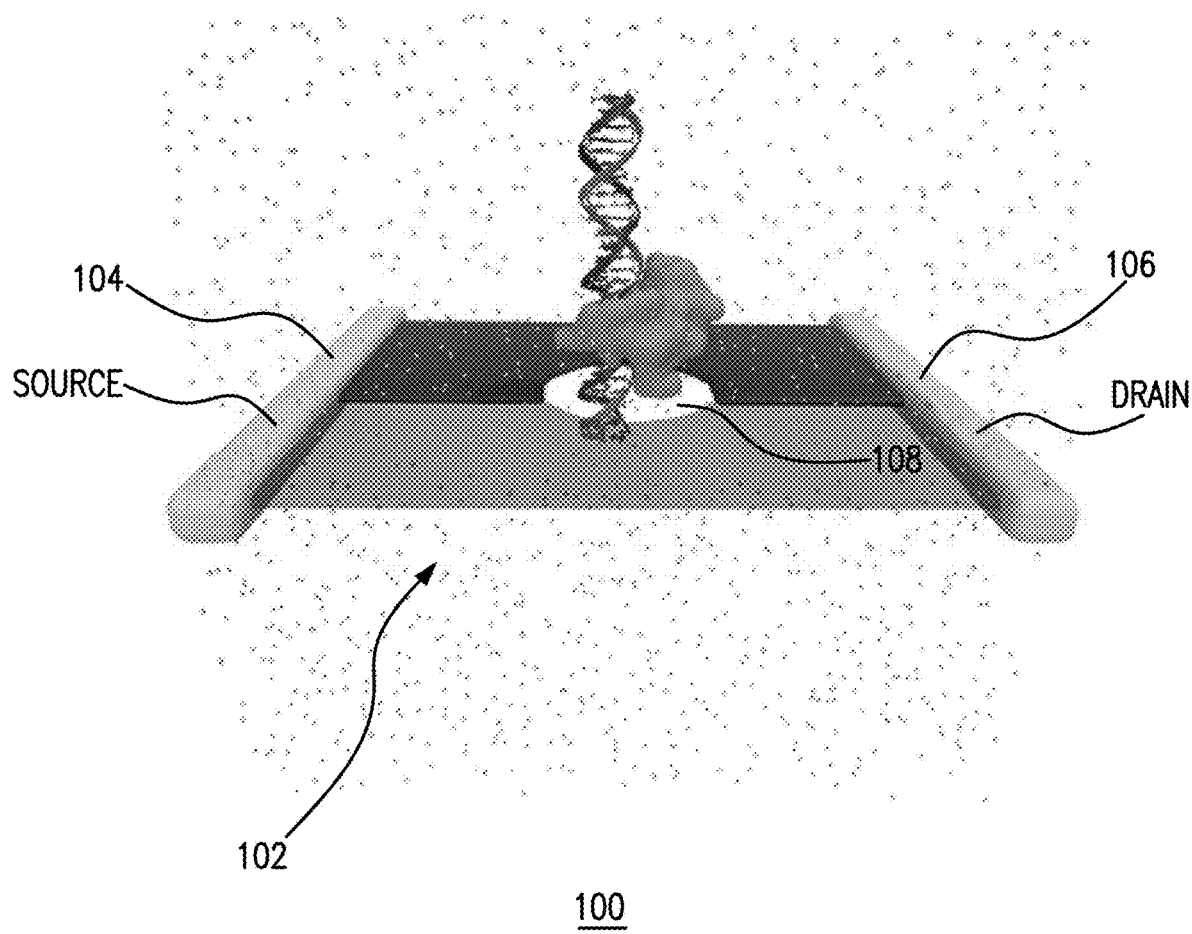
FIG. 1A depicts a schematic of a multifunctional 2D semiconductor material (e.g., graphene or $MoS_2$) according to an embodiment that is utilized for the detection of methylated sites along the DNA. Distinct peaks in the transverse conductance and dips in ionic current are indicative of methylated site translocation.

In various embodiments, the electronic properties of 2D solid-state nanopore materials can be used to provide a versatile and generally applicable biosensor technology. The biosensor technology can be facilitated via use of a combination of molecular dynamics, nanoscale device simulations, and statistical signal processing algorithms.

As described herein, a case study is directed to the classification of three epigenetic biomarkers (methyl-CpG binding domain 1 (MBD-1), MeCP2, and γ-cyclodextrin) attached to double-stranded DNA to identify regions of hyper-methylations and/or hypo-methylations by utilizing a matched filter. Assessed is the sensing ability of the nanopore device to identify the biomarkers based on their characteristic electronic current signatures. Such a matched filter-based classifier can enable real-time identification of the biomarkers that can be implemented on chip. In various embodiments, this integration of a sensor with signal processing architectures can enable a multipurpose technology for early disease detection.

As described herein, various embodiments can provide an integrated approach that combines electronic simulation based on device physics with statistical signal processing techniques to characterize the resolution limit of solid-state nanopore sensing and to facilitate provision of algorithms for epigenetic marker classification.

As described herein, various embodiments can provide a sensor technology that is capable of detecting and mapping (across the genome by utilizing bulky biomarkers) one or more regions of hyper-methylations and/or one or more regions of hypo-methylations. In various examples, these biomarkers can be further classified using electronic sheet currents resulting from electrically active 2D nanopore membranes (because each marker produces a current signature unique to its structure and spatial charge distribution).

Among bulky groups to label methylated cytosines along a double-stranded DNA, utilized (in various examples) can be either methyl-CpG binding domain (MBD-1) protein or methyl CpG binding protein 2 (MeCP2) to identify regions of hypermethylation. In humans, these two proteins bind to regions of hypermethylation along the DNA and are thought to repress transcription from methylated gene promoters (see Reference 17A). Abnormal levels of MBD protein and their polymorphisms have been associated with the overall risk of lung cancer (see References 18A, 19A). Furthermore, MeCP2 mutations are thought to be responsible for Rett syndrome, a severe neurodevelopmental disorder. The expression of MeCP2 in the brain is mostly in mature neurons and therefore can play a role in the identification of neurological diseases. Analogously, to identify regions of hypomethylation, considered herein (in various examples) is the detection of unmethylated CpGs marked by γ-cyclodextrin (GCD). This synthetic biomarker can be used to identify hypomethylated sequences, similar to the approach described by Gilboa et al. (see Reference 15A).

FIG. 1A illustrates, according to an embodiment, a model setup 100 utilized to obtain the electronic current signatures for epigenetic marker proteins. The setup consists of a 2D material (see generally call out number 102) connected between two electrodes, that is, the source 104 and drain 106 to enable the flow of current through the membrane 102 under an applied bias. In various examples, the membrane 102 can comprise graphene, $MoS_2$, or other transition-metal dichalcogenide membranes. The detection sensitivity of the membrane 102 is controlled via a gate electrode separated from the membrane 102 by a high-κ dielectric (not shown). A circularly shaped nanopore 108, chosen to have a diameter (for example) of 5 nm, allows the translocation of the biomolecule through the membrane 102. This dimension of 5 nm is about the smallest pore diameter through which the DNA-marker complex can translocate without any hindrance. The whole setup is (in this example) immersed in water containing a 1M electrolyte of potassium chloride (KCl). A DNA strand, complexed with a marker protein either at the methylated cytosine site (for hyper-methylation) or at unmethylated adenine (for hypo-methylation), is translocated through the nanopore 108 using an applied bias across the cis and trans chambers (VTC). Modulation in current flowing through the membrane (sheet current) enables calibration of the local electrostatic potential distribution within the nanopore at a given time instant.

Figure 1B:
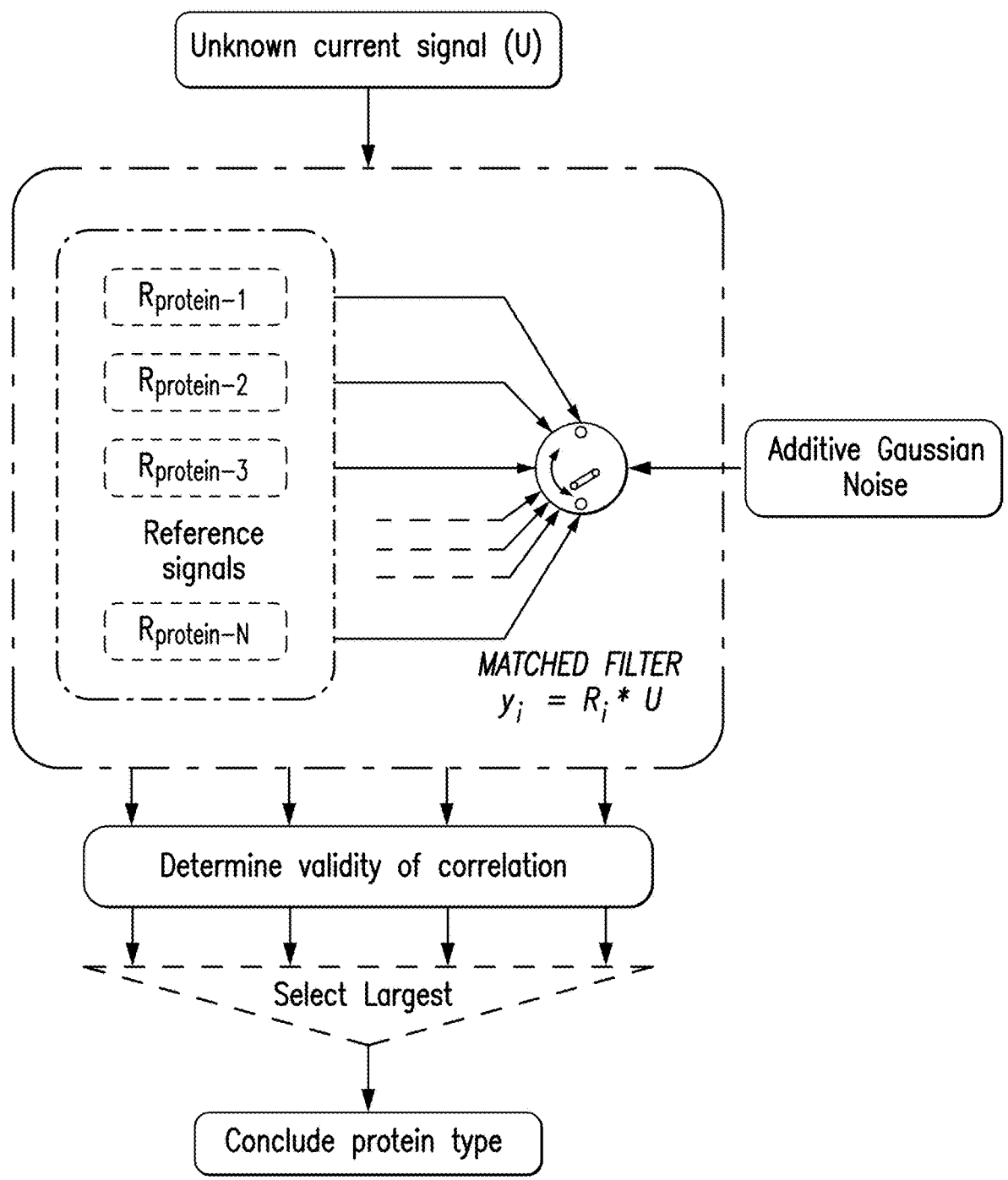
FIG. 1B depicts a schematic of a matched filter-based detection workflow according to an embodiment whereby the type of marker protein on a DNA is determined using correlation between the noisy input signal (test signal) and a dictionary of precomputed reference current signatures from "noise-free" translocation of DNA-marker complexes.

For a statistical analysis according to an embodiment, needed are signal references that are obtained from frozen DNA current signatures, where the biomolecule is artificially translocated through the pore in the absence of all-atom molecular dynamics (MD) simulations, as previously performed by Girdhar et al. (see Reference 11A) The noisy test signal is obtained from a computation scheme involving MD simulations coupled to semiconductor device models (see Reference 14A). A detailed description of MD system setup, simulation methodology, and electronic transport calculations are discussed below. In the noise-free reference signal, the observed current from the DNA-marker complexes will arise solely from the charge distribution across the proteins, which are unique to the protein structures themselves. The set of these noise-free signals will comprise a set of unique reference current signatures for epigenetic markers. Once this reference set is built, it can be used to identify the type and/or number of proteins by a statistical signal processing algorithm such as a bank of matched filters, as outlined in FIG. 1B. As seen in algorithm 200 of FIG. 1B, reference signals for each of the marker proteins are denoted as $R_i(t)$, where i is the marker protein. An unknown noisy signal (denoted as U), obtained by MD simulations, where the marker protein is unknown, is input into the filter bank that classifies the marker-protein type depending on correlations between the unknown current signal and reference signals (various embodiments described herein utilize data (such as electrical characteristics associated with DNA moving through a nanopore) that are obtained via simulations; such embodiments can, of course, alternatively be implemented via use of actual measured data (such as actual measured electrical characteristics associated with DNA moving through a nanopore)).

In this context, it is known that the optimal filter for detecting pulses in the presence of additive white Gaussian noise is the matched filter (see References 20A-22A) (a similar model describing ionic currents in the presence of wide-band Gaussian noise was used for translocation event detection (see Reference 23A)). It can further be shown that the probability of detecting a weak signal in the presence of noise is largest when the signal-to-noise ratio is also largest (see Reference 24A). Because the matched filter output is just the correlation with the reference signal, circuit implementations (see References 22A, 25A) in nanoscale computing technologies can be implemented.

In the presence of additive colored noise, for example, 1/f noise rather than white noise, one would have a whitening prefilter followed by designing the matched filter for the whitened reference signal. A noise model of one embodiment considers only the low-frequency regime of detection, that is, <100 kHz. When the sampling rate is increased toward mid- and high-frequency regimes, different noise models need to be considered and the corresponding matched filter implementations will be modified. Mid-frequency will mainly consist of thermal noise, whereas the high-frequency regime will be dominated by capacitance effects. Power spectral densities for the different frequency regions are outlined by Parkin et al. (see Reference 26A).

Using such a matched filter-based detection method, provided herein is a unified framework to detect, classify, and count multiple marker proteins along the DNA (this unified framework can also build upon the dictionary of reference signals).

In various embodiments, the reference signatures for each of the biomarkers were calculated for noise-free trajectories on graphene and $MoS_2$ quantum point contact nanoribbons. Additionally, another important aspect of the respective current signature is the shape of the trace because the magnitude depends on the stochastic fluctuation of the complex and its spatial orientation within the pore. In this regard, it has been previously shown that during the translocation of a methylated DNA complexed with either one or two MBD-1 protein complexes, depending on the number of methylated sites, the conductance square deviation is drastically different due to the strong dependence of the sheet conductance on the angular position of the marker protein within the pore (see Reference 13A).

Once the reference current signatures are obtained, a correlation of a current signal consisting of an unknown marker with each of the reference signals will identify the type of marker protein. Given a reference signal $r_i(t)$ and a signal of an unknown marker u(t), the cross-correlation is given as $$\rho(t) = \int_{-\infty}^{\infty} r_i(\tau)u(t+\tau)d\tau \quad (1)$$

To capture just the shape of a signal and compare signals due to different marker proteins across various orientations, normalized are the correlation signals to range between −1 and 1. Given a correlation trace $\rho(t_i)$, where $t_i$ is the sampled time instant, the normalized current trace is given by $$\rho_{norm}(t_i) = \frac{\rho(t_i) - \rho(t_{open})}{\max(\rho(t)) - \min(\rho(t))} \quad (2)$$

Here max($\rho(t)$) and min ($\rho(t)$) denote the maximum and minimum values of the calculated trace during the translocation period during which the signal was acquired. This normalization allows comparison of the different correlated signals irrespective of their angular position during translocation. Specifically, the criterion used to infer the type of marker protein from the correlated signal is the Q factor defined as $$Q = \frac{1}{BW_{corr}} \quad (3)$$

where $BW_{corr}$ is the bandwidth of correlation between the test and a particular dictionary signal. The value of correlation chosen to estimate the bandwidth is a hyperparameter (i.e., chosen by the user, based on statistics of different calculations, usually ranging from 0.6 to 0.8, as indicative from various example calculations). In these sets of simulations, the $BW_{corr}$ has been chosen to be calculated at $\rho_i$=0.70, where $\rho_i$ denotes the correlation between the test and reference signal of protein i (MBD, GCD, MeCP2). These hyperparameters are nonphysical quantities that can be fine-tuned by obtaining statistics of multiple translocations of the proteins with different configurations and initial conditions. Essentially, once the correlations between the test and dictionary signals have been computed, the protein whose current signature provides the maximum Q factor is inferred to be present along the DNA.

Figure 2:
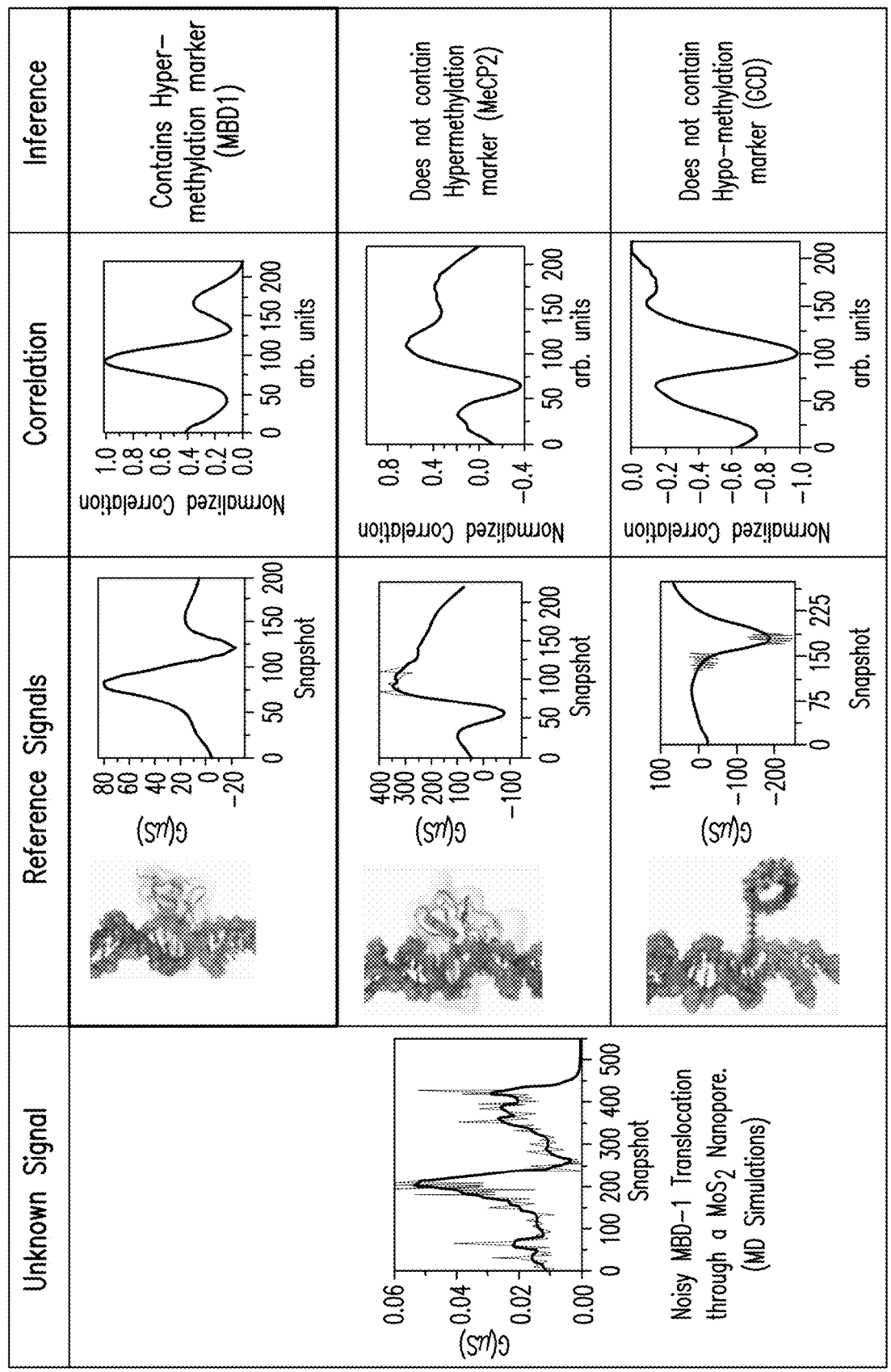
FIG. 2 depicts classification of epigenetic biomarkers according to an embodiment. The set of reference signals (second column from the left) in this example is determined by computing the sheet current signatures corresponding to translocations of frozen DNA-MBD, DNA-MeCP2, and DNA-GCD complex through a 5 nm $MoS_2$ nanopore. A noisy current trace for the nonideal translocation of a DNA-MBD complex containing one MBD1 protein (as shown in the leftmost column) is correlated with each of the entries in the dictionary. A peak is observed when correlated with the frozen signature of a DNA-MBD complex with one protein (top row, second column from the right and the rightmost column) and no discernible peaks when correlated with the other current signatures. The corresponding Q factors calculated at $\rho=0.7$ are maximum for the correlation of the unfrozen DNA-MBD complex with the current signature of the MBD protein, indicating the presence of a MBD1 protein along the methylated DNA.

FIG. 2 illustrates the utility of the Q factor as a metric to infer the presence or absence of a particular protein along a translocating DNA. In these simulations, the test signal is obtained from translocating a 30 bp long DNA complexed with a single MBD1 protein at a CpG site. This test signal is noisy because it is obtained from calculating the current trace along the MoS$_2$ membrane from the resulting trajectory of an all-atom MD simulation. As shown in FIG. 2, the first (leftmost) panel indicates the noisy current signature of the translocating MBD1 protein, whereas the second panel (from the left) displays the normalized current signatures (top to bottom) from MBD-DNA, MeCP2-DNA, and GCD-DNA complexes, respectively. The noisy current signal (on the leftmost panel) was obtained from a previous work (see Reference 14A). As mentioned, the second panel (from the left) consists of the calculated current traces during a noise-free translocation of a DNA complexed with a MBD1, MeCP2, and GCD marker protein, respectively. The third panel (from the left) illustrates the matched filter operation between the noisy signal and the respective reference signals normalized to the interval [−1, 1]. The Q factor is calculated at ρ=0.7, resulting in a value of 0.023 for the MBD1 reference signal. For the MeCP2 and GCD correlations, the Q factor is 0 because the maximum value of the cross-correlation signal is <0.7. It is therefore evident (in this example) that the Q factor of the correlated outcome between noisy DNA-MBD and that of current signature of MBD is the highest, indicating the presence of the MBD protein along the DNA and the corresponding absence of the GCD or MeCP2markers.

Figure 3A:
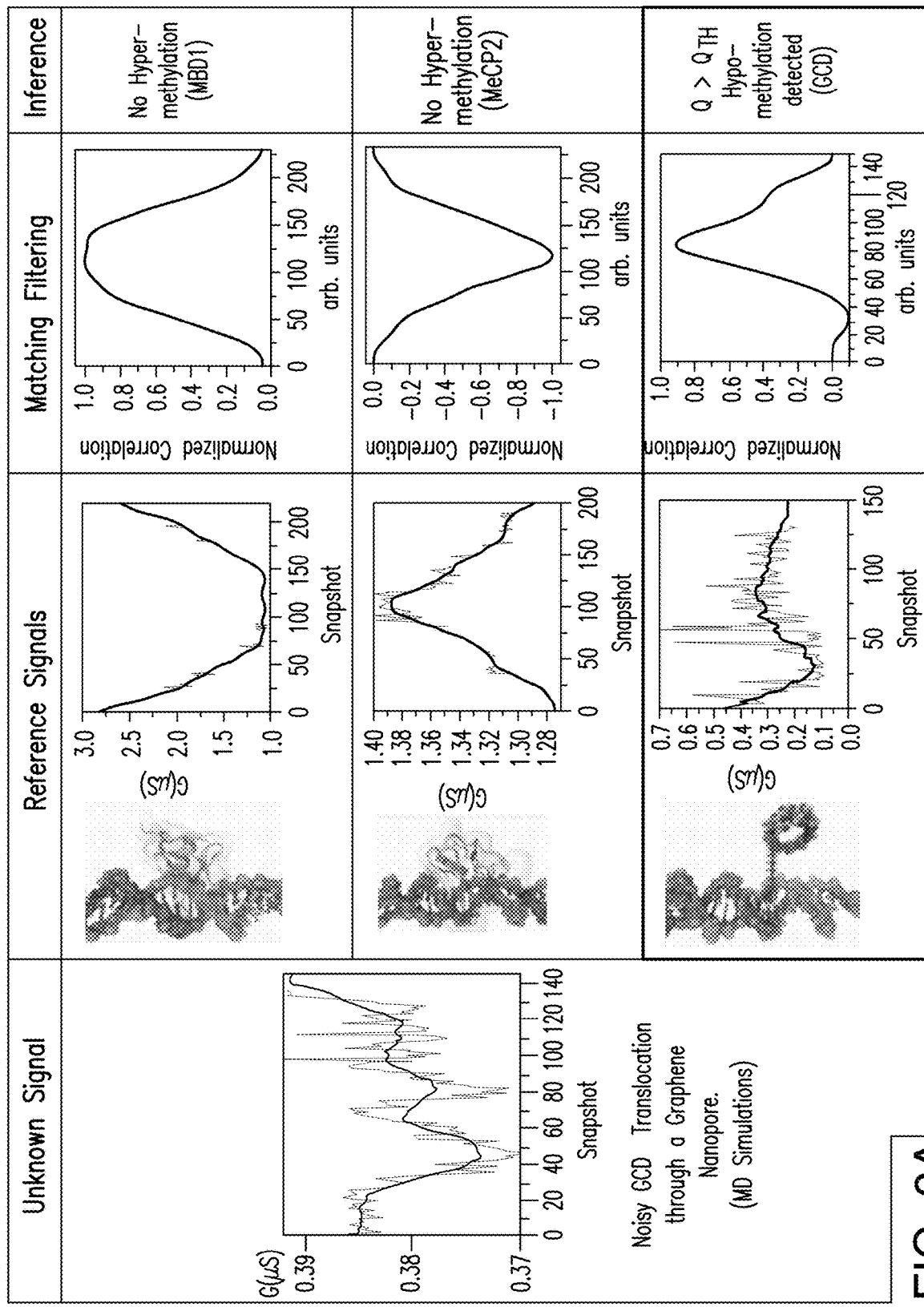
FIGS. 3A and 3B depict matched filter operations according to an embodiment to classify regions of hyper-methylation biomarkers and hypo-methylation biomarkers along a DNA translocating through graphene nanopores.
Figure 3B:
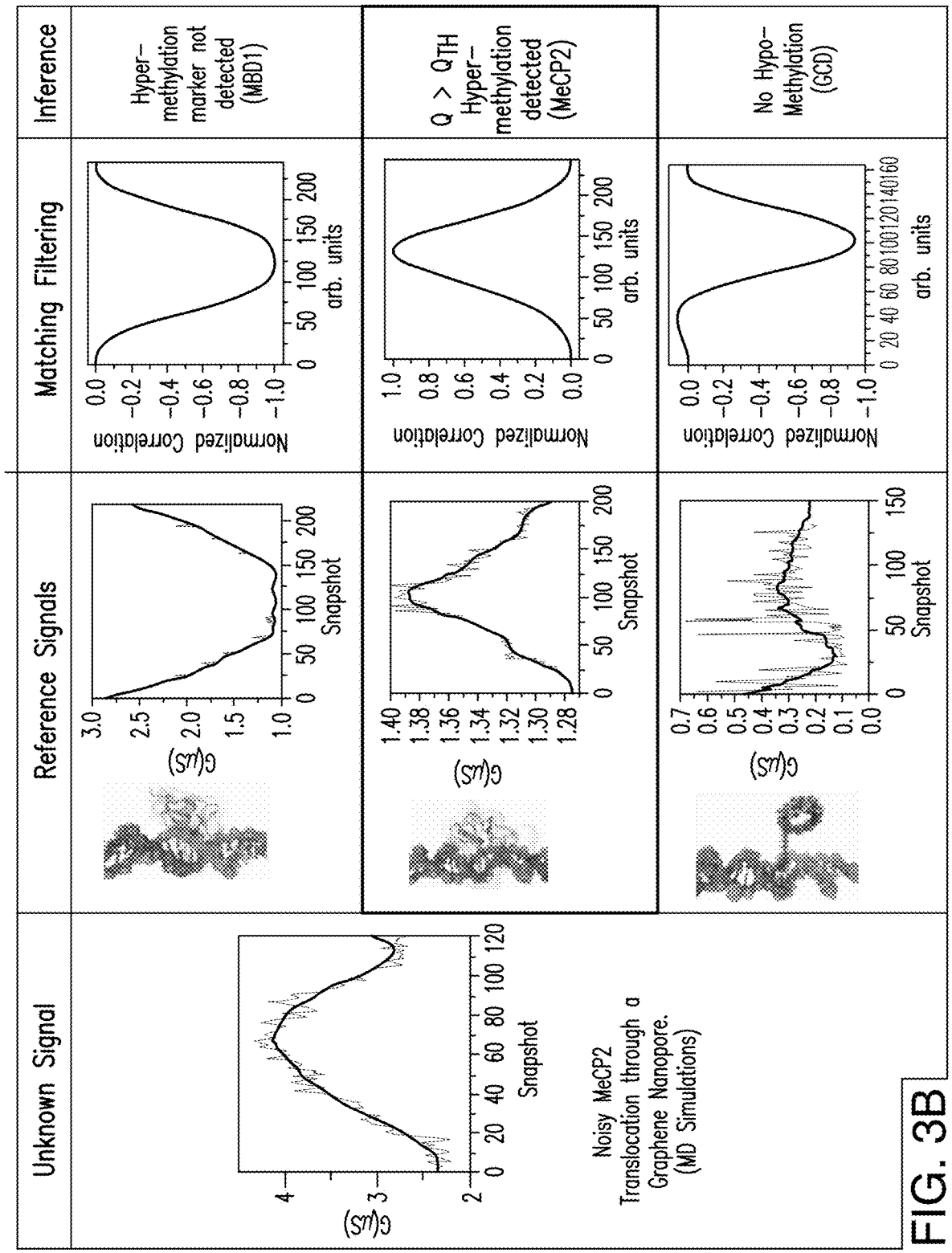

To illustrate the generality of this approach, further illustrated is example classification of the marker groups with unknown and reference signals calculated from translocations in graphene nanopores. FIGS. 3A, 3B illustrate the normalized correlations obtained between a noisy signal of a DNA complexed with hypo-methylated (GCD) and hyper-methylated (MeCP2) epigenetic biomarkers, respectively. In FIG. 3A, the reference transverse current signatures (top to bottom) for MBD1, MeCP2, and GCD are shown in the second panel (second from the left), whereas the corresponding normalized correlations between the noisy unknown signal and the reference signals are shown in the third panel (from the left). One can clearly see that the correlation of the noisy signal corresponding to the GCD biomarker with the GCD reference signal gives the sharpest peak and greatest Q factor at ρ=0.7 of ~0.04, whereas the Q factors corresponding to correlations with the MBD1 and MeCP2 markers are ~0.017 and 0, respectively. Similarly (see FIG. 3B), a noisy translocation of a DNA-MeCP2 complex yields the maximum Q factor of ~0.018 at ρ=0.7 when correlated with the reference signal of a MeCP2 biomarker. Therefore, these results indicate the versatility of the approach in developing a set of reference signals and classifying the unknown epigenetic biomarker using the matched filter.

Figure 4:
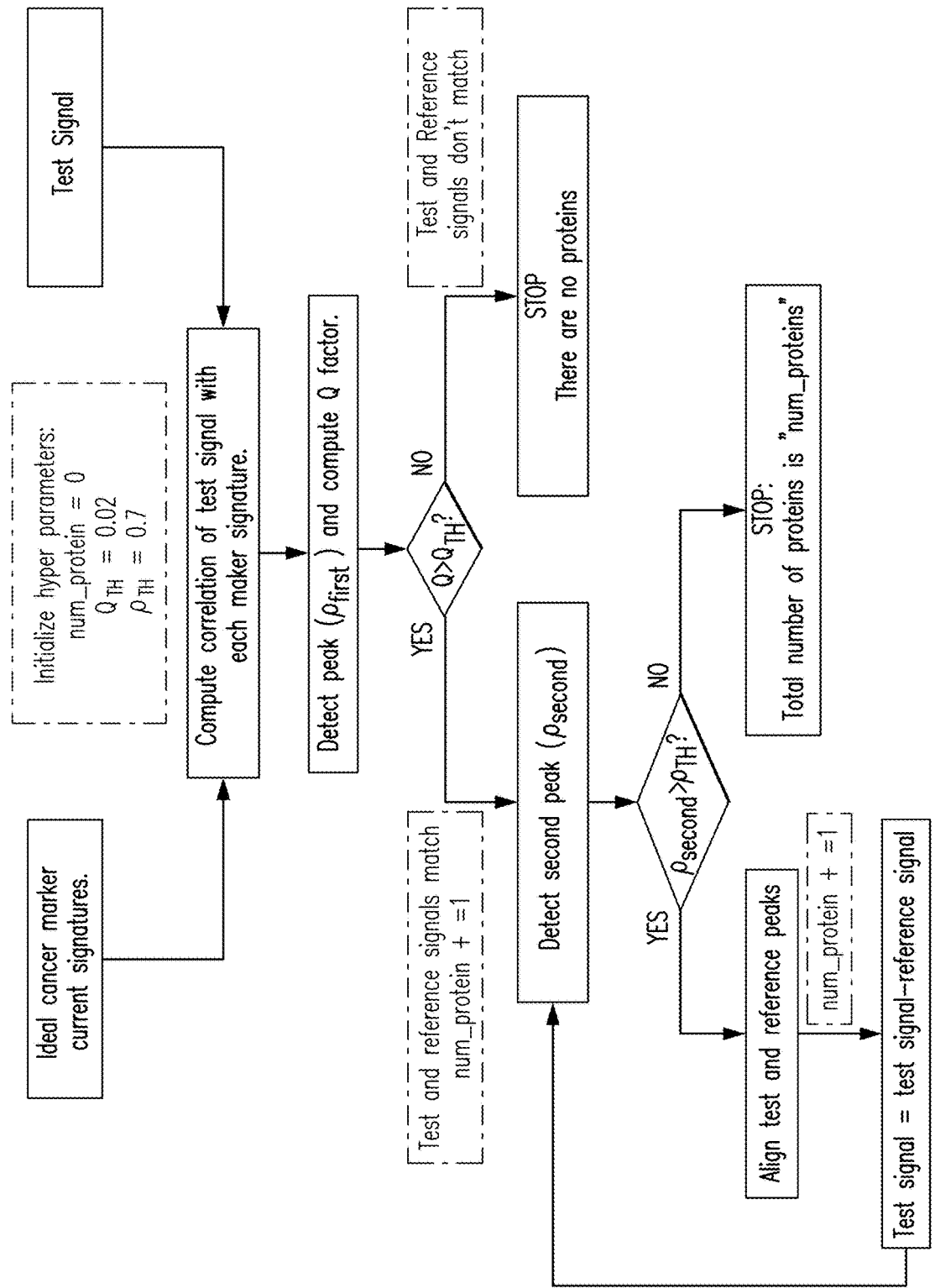
FIG. 4 depicts a flowchart illustrating an algorithm according to an embodiment to detect the type of marker protein and the count of the number of markers in the vicinity of the protein recursively. The hyperparameters chosen are the threshold Q factor and the threshold correlation value that decide the hypothesis of whether a particular marker and vicinity markers are present, respectively. Furthermore, this procedure of detecting and counting the marker proteins can be computed recursively and implemented (for example) in hardware.

The approach described above illustrates the use of the matched filter algorithm to classify particular epigenetic markers. This matched filter can be applied in any setting, but it can be proven to be the optimal linear detector in the presence of additive noise. Additionally, the Q factor alone can be used as a metric to infer the hypothesis of whether the particular type of protein is present or absent. However, to simultaneously detect, infer, and count the type and number of proteins, illustrated herein is an algorithm that is capable of automatically deciding the validity of a marker and also counting the number of surrounding markers in its vicinity recursively. This unified algorithm according to an embodiment is shown in FIG. 4. In this algorithm, utilized are two hyperparameters denoting the threshold value ($Q_{TH}$) of the Q factor, indicating the validity of the particular hypothesis, that is, to make the decision of whether the vicinity protein is present or absent, and a threshold correlation coefficient ($\rho_{TH}$), indicative of the presence of the second protein in the vicinity.

This algorithm according to an embodiment has two inputs: the dictionary of signals (see the block in FIG. 4 labeled "Ideal cancer marker current signatures.") from the various epigenetic cancer markers (in this example, MBD1, MeCP2, and GCD) and a test signal (see the block in FIG. 4 labeled "Test Signal") from a DNA complex with an unknown marker protein. These two above-mentioned blocks in FIG. 4 feed into the block labeled "Compute correlation of test signal with each marker signature". Also, as shown in FIG. 4, prior to the computing of the correlation, a number of hyper parameters are initialized in this example as follows: num_protien=1; $Q_{TH}$=0.02; $\rho_{TH}$=0.7. Initially, the normalized correlation and corresponding Q factors between the test and dictionary current signatures are calculated (see the block in FIG. 4 labeled "Detect peak($\rho_{first}$) and compute Q factor."), the maximum of which indicates the identity of the marker protein. As seen in the block of FIG. labeled "Q>$Q_{TH}$", a "NO" leads to a "STOP" (Test and Reference signals don't match) and a "YES" leads to "Detect second peak $\rho_{second}$" (Test and reference signals match; num_protien+=1). The second peak in the calculated correlations is also simultaneously monitored (see the block in FIG. 4 labeled "Detect second peak $\rho_{second}$") to infer the presence of another marker in the vicinity. If the value of the second correlation peak ($\rho_{second}$) is greater than $\rho_{TH}$ ("YES"), then the correlation is indicative of a second marker protein of the same type present in the vicinity (if "NO", then "STOP: Total number of proteins is 'num_protiens'"). Next considered are the normalized correlations between the frozen single DNA-marker complex and the noisy signals from the translocation of the DNA with a single complex (known as reference correlation) and multiple complexes (of the same type such as MBD/GCD). When these correlation peaks are aligned (see the block in FIG. 4 labeled "Align test and reference peaks"), a difference between them (see the block in FIG. 4 labeled "Test signal=test signal−reference signal") will result in the presence of a peak (num_protien+=1). From this stage onward, the value of the second peak is recursively monitored, while subtracting the reference correlation at each iteration. The value of $\rho_{second}$ is used to determine the presence or absence of a marker-protein in the vicinity depending on a hyperparameter threshold value ($\rho_{TH}$). This process of detecting and determining the value of the second peak from the subtracted signal can be performed recursively until the hypothesis is no longer valid.

Figure 5:
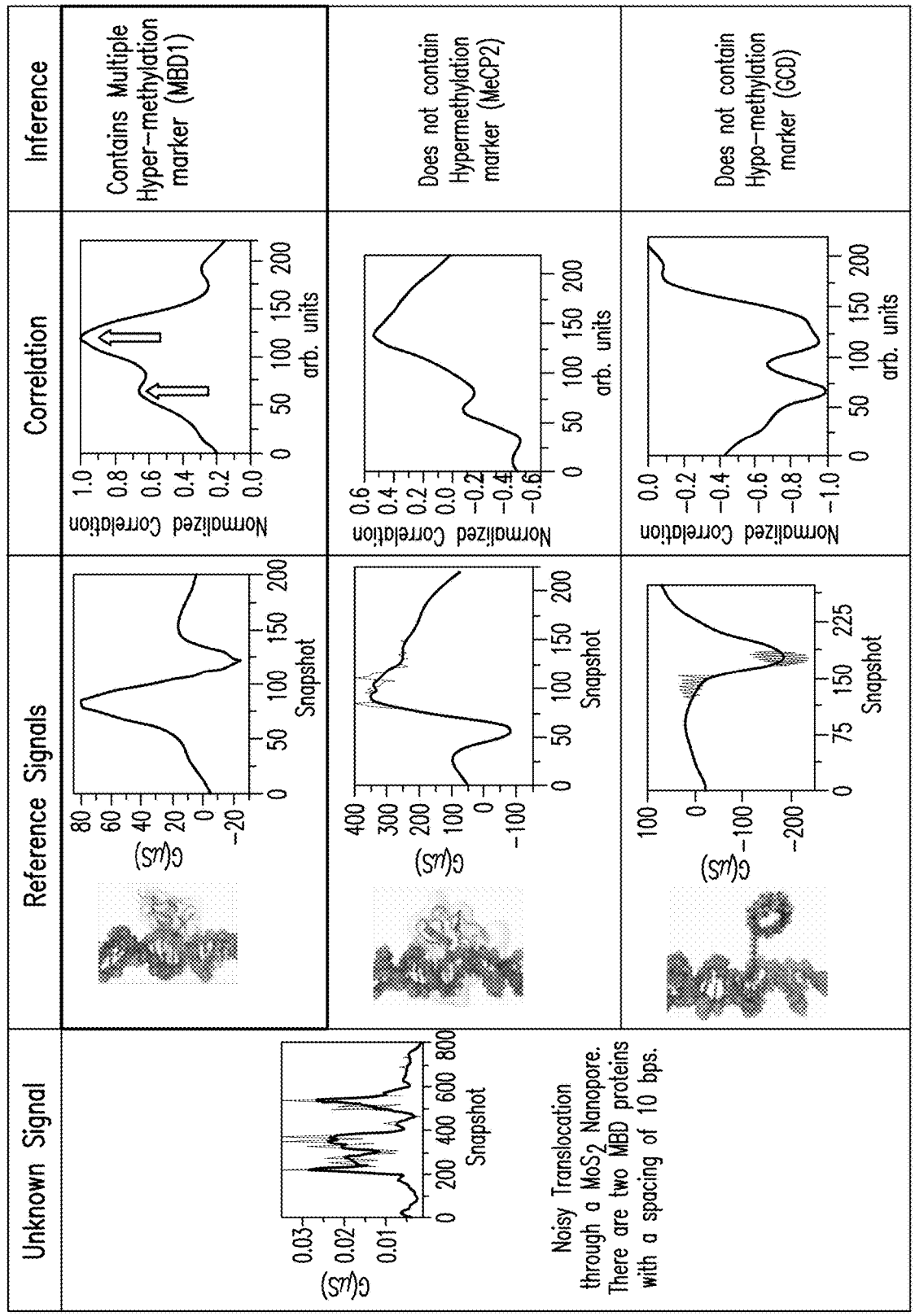
FIG. 5 depicts detecting multiple proteins according to an embodiment. A noisy current trace of a DNA strand containing two MBD1 proteins (as shown in the leftmost column) is correlated with each of the entries in the dictionary. In this example, two peaks are observed when correlated with the frozen DNA signature of a DNA-MBD complex with one protein (top row, second column from the right and the rightmost column). The absence of such a peak from the correlation of the noisy signal with the other frozen DNA-marker complex signals indicates the presence of an MBD protein in the measured noisy signal.

The algorithm illustrated in FIG. 4 can be utilized to detect and count multiple proteins complexed to a DNA, as shown in FIG. 5. In this simulation scenario, considered are a 60 base pair (bp) long DNA strand that consists of two methylated CpG sites that are separated by 10 bp's. Each of these individual CpG sites are complexed by MBD1 proteins. The reason that the spacing of 10 bps is chosen in this example is due to the physical dimensions of the label protein MBD1 being 10 bp's wide, making 10 bp's the minimum possible distance that the two labeled sites can be present without mutual steric hindrance from the labels. This unconstrained DNA-MBD complex is translocated to obtain the noisy signal, as shown in the leftmost column of FIG. 5. This normalized current signature of two MBD1 proteins located 10 bp's apart was previously obtained (see Reference 14A).

The plot of the correlation between the noisy two-protein signal and the reference signals for DNA-GCD or DNA-MeCP2 complexes does not display a discernible peak, indicating a lack of similarity between the dictionary signal entry and the measured noisy signal. On the contrary, correlating the noisy two-protein signal with the frozen single-protein signal (third panel from the left, first row) yields two peaks that could correspond to the similarity of features between each of the individual protein signatures and the single protein dictionary entry. The second peak of the correlated signal is greater than the threshold, indicating the possible presence of the second protein.

Figure 6:
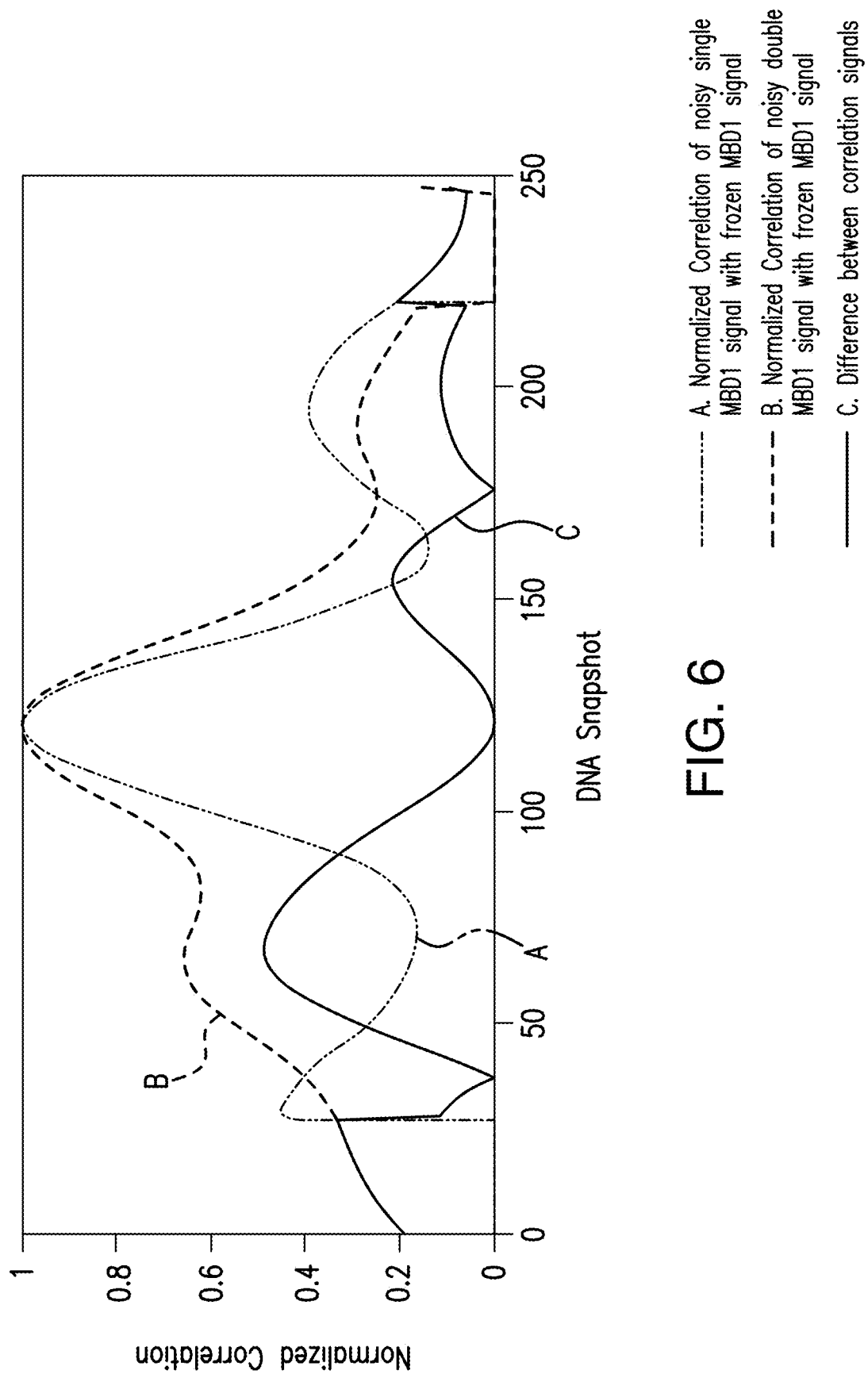
FIG. 6 depicts counting the number of proteins according to an embodiment. In this example, to count the number of proteins, considered are the normalized correlations between the frozen single MBD-DNA complex and the noisy signals from the translocation of the DNA with a single-MBD (curve "A") and multiple-MBD (curve "B"). A difference (curve "C") between the two aligned correlation peaks results in the presence of a peak, the value of which can be used to determine the presence or absence of the second protein depending on a preset threshold value.

The validity of the presence of the second protein can also be determined according to the recursive matched filter algorithm shown in FIG. 4. To count the number of proteins, utilized are the correlations as shown in FIG. 5, where the normalized values of the frozen single-protein current signatures (see the second column from the left) with the noisy two-protein signal (see the leftmost column) are plotted. As shown in the algorithm, monitored is the value of the second peak to determine the presence of the second protein. Because $\rho_{second} > \rho_{TH}$ peaks between the two normalized signals (correlated and reference correlation signal) are aligned and subtracted, the height of $\rho_{second}$ can be examined in the resulting curve (curve "C"), as shown in FIG. 6. Because the second peak of the curve "C" is less than $\rho_{TH}$, it is concluded that only two proteins are present.

This algorithm can be performed recursively for counting multiple proteins in the vicinity. In one specific example, the real-time detection and classification of epigenetic biomarkers from a time series of current data could involve a combination of event detection similar to the approaches utilized by nanopolish in Oxford Nanopore's MinION basecaller (see Reference 27A) applied to solid-state nanopores. It is believed that the nanopolish approach can currently count the quantity of marker proteins in the vicinity only if they are of the same type. In another embodiment, the algorithm can be generalized to detect different marker proteins within the resolution limit by checking if $\rho_{second}$ correlates with the dictionary signals (this approach is sensitive to the choice of hyperparameters, which need to be chosen specifically depending on the dictionary signals obtained and can be fine-tuned depending on the set of protein signatures available).

As described herein, considering signals from solid-state nanopore devices, an algorithm has been provided to determine the type of marker proteins and to simultaneously identify the possible epigenetic markers in the vicinity. This approach has been illustrated to detect and identify the presence of different biomarkers corresponding to hypo-methylation and/or hyper-methylation within a limited set of dictionary signals. While the approach has not yet been tested on experimental traces (for which there are certain technical difficulties related to fabrication and electric measurements in the nanopore devices (see Reference 28A)), various implementations using actual traces are, of course, within the scope of this disclosure.

In other embodiments, the algorithm can be expanded to include an exhaustive set of current signatures for various epigenetic markers calculated from different sensing materials. This approach can also be generalized to incorporate signals from different noise models in the matched filter algorithm. Further, an embodiment of the algorithm using matched filter banks can be implemented in hardware (see References 24A, 25A) which can enable a DNA sensor chip consisting of a highly dense array of nanopores (see Reference 29A) with sensing and inference logic realized on the same wafer.

Reference will now be made to a detailed discussion of an example molecular dynamics simulation protocol to obtain noisy current signatures followed by the electronic-transport model description for graphene and $MoS_2$ nanopore membranes to obtain the sheet currents of the biomarkers translocating through the nanopores.

To obtain the noisy current signatures of the DNA-marker translocations, all-atom MD simulations were run using the latest version of NAMD (see Reference 1B). Each system is built, visualized, and analyzed using VMD software (see Reference 2B). The methyl-binding proteins MBD1 (PDB code: 1IG4)(see Reference 3B), MeCP2 (PDB code: 3C2I) (see Reference 4B) for hyper-methylation and γ-cyclodextrin(GCD) (see Reference 5B) for hypo-methylation are described using CHARMM22 force field with CMAP corrections (see Reference 6B). The DNA molecule structure is obtained using 3D-DART server (see Reference 7B) and described using CHARMM27 force field (see Reference 8B).

The carbon atoms comprising graphene are treated as CA atoms and described using CHARMM27 (see Reference 8B). For the $MoS_2$ membrane, the atoms are spatially fixed requiring only the non-bonded interaction parameters which are obtained from Stewart et al. (see Reference 9B).

The nanopore membrane along with the DNA-marker complex is immersed in a water box, where the water molecule is modeled as TIP3P model (see Reference 10B). Ions $K^+$ and $Cl^-$ are placed randomly in the water box to achieve a uniform concentration of 1 M. The particle-mesh Ewald method is used for long-range electrostatic interactions (see Reference 11B). Van der Waals energies are calculated using a 12 Å cutoff. Each system is minimized for 5000 steps. Once the minimization converged considerably, equilibration using the minimized parameters is performed for 0.6 ns as an NPT ensemble. During the equilibration, the system is maintained at a constant pressure of 1 atm using Langevin piston (see Reference 12B). After equilibration, an external field $\varepsilon = V/L_z$ is applied along the +z direction to drive the DNA-protein complex through the nanopore, where V is the voltage bias and $L_z$ is the length of the water box along the z direction. During the simulation, the atoms rearrange to produce the actual non-uniform potential across the 2D membrane (see Reference 13B). The actual potential is the sum of potential induced from the simulated charges plus the applied voltage. During the simulation, a constant temperature of 300 K was maintained using a Langevin thermostat. For some cases, to ensure successful translocation of the molecule within a reasonable amount of time, a small force of 1 kcal/mol/Å in the −z direction is applied to the backbone of the DNA molecule using tclForces. While these tclForces allow for successful translocations, an embodiment of the matched filter algorithm for epigenetic detection described herein is based on the transverse sheet current signatures. These signatures remain unaffected by the force used to drive the molecule through the nanopore, as the sheet current is influenced only by the potential induced by the DNA-marker complex around the pore and not the rate of translocation.

Once the translocation of the DNA-protein complex is completed using MD simulations, a trajectory file of all the molecules of the system driven through the nanopore under the influence of electric field is obtained. The transverse currents are calculated simultaneously for each of the given trajectory of the DNA-marker complex. The first step of this methodology involves calculating the electrostatic potential using a non-linear Poisson Boltzmann formulation. The rationale and detailed description of the methods used are outlined by Girdhar et al. (see Reference 11A). Briefly, given a trajectory of the DNA-marker complex described at preset time intervals, the electric potential φ(r) is calculated for each position using the Poisson equation (see References 4A and 14B-15B):

$$\nabla \cdot [\epsilon(r) \nabla \varphi(r)] = -e[K^+(r) - Cl^-(r)] - \rho_{DNA}(r) \quad (4)$$

where $\rho_{DNA(r)}$ is the charge due to the DNA-marker complex. The charges due to the solute ions, potassium ($K^+(r)$) and chlorine ($Cl^-(r)$) were described assuming Boltzmann equilibrium, namely, $$K^+(r) = C_0 \exp\left[\frac{-e\varphi(r)}{k_B T}\right], \quad (5)$$

$$Cl^-(r) = C_0 \exp\left[\frac{e\varphi(r)}{k_B T}\right]. \quad (6)$$

Here, K+ and Cl⁻ are the local ion concentrations and $C_0$ is the nominal concentration in the solution which has been set to 1 M. Equations (5) and (5) were solved iteratively until convergence.

Using the electric potential φ(r) calculated by Poisson Boltzmann equations, the Green's function given by equation (7) is computed using the non-equilibrium Green's function formalism.

$$G = \left[(E + i\eta)I - H - \sum_\alpha \sum_\alpha\right]^{-1} \quad (7)$$

where $\Sigma_\alpha \equiv V_{\alpha C}^\dagger [E - H_\alpha]^{-1} V_{\alpha C}$ is the "self energy" of lead α and I is the identity matrix. Here, H, the tight-binding Hamiltonian is used to characterize the electronic transport through each carbon atom in the defined nanopore membrane lattice (see Reference 11A). Implemented is the third nearest neighbor and three orbital interactions in the Hamiltonian.

Using G, obtained is the transmission coefficient T(E) between leads 1 and 2 given as:

$$T(E) = -\text{Tr}[(\Sigma_1 - \Sigma_1^\dagger) G (\Sigma_2 - \rho_2^\dagger) G^\dagger]. \quad (8)$$

Finally, the transverse conductance at the source-drain bias $V_{SD}$ is calculated using equation (9).

$$G = \frac{2e}{V_{SD} h} \int_{-\infty}^{\infty} T(E)[f_1(E) - f_2(E)] dE \quad (9)$$

Here, $f_\alpha(E) = f(E - \mu_\alpha)$ is the probability of an electron occupying a state at energy E in the lead α, and $V_{SD} = (\mu_1 - \mu_2)/e$ is the bias across the conductor. All conductances across graphene membranes were obtained at a Fermi energy of 0.05 eV.

In order to obtain the transverse sheet currents in $MoS_2$ quantum point contact nanopore membranes, the electronic transport through $MoS_2$ is formulated as a self-consistent model based on the semi-classical thermionic Poisson-Boltzmann technique using a two-valley model within the effective mass approximation. A detailed discussion of the model and its implications on the pore size and position are outlined by Sarathy et al. (see reference 1C).

Briefly, the conductance calculated from the thermionic current flowing from the source to drain through a particular mode at a given voltage is described as $$G_{n_{1,2}} = \frac{2e^2}{h} \frac{1}{1 + \exp\left(\frac{E_{n_{1,2}}^K - E_F^L}{k_B T}\right)} + \frac{2e^2}{h} \frac{1}{1 + \exp\left(\frac{E_{n_{1,2}}^Q - E_F^L}{k_B T}\right)}. \quad (10)$$

Here $E_F^L$ is chosen as the energy level reference set up on the left side of the membrane, $n_{1,2}$ represents the energy mode at the particular channel, and $E_{n_{1,2}}^K$ and $E_{n_{1,2}}^Q$ are the energy levels at a particular channel and mode due to the effective masses at K and Q, respectively. The total conductance is the sum of the conductances through all modes in the channels.

The linear response of the electronic conductance at a particular energy mode $n_{1,2}$ in the presence of the DNA external potential near the pore is given by $$\langle G_{n_{1,2}} \rangle = \sum_{i=[K,Q]} \frac{dG_{n_{1,2}}}{dE_{n_{1,2}}^i} \langle e\varphi_{DNA} \rangle_{n_{1,2}}. \quad (11)$$

The total variation (δG) in conductance with respect to conductance of the empty pore is the sum of individual variations due to each energy mode in each channel. The quantity $\langle e\varphi_{DNA} \rangle_{1,2}$ represents the spatially averaged value of external potential due to the DNA ($\varphi_{DNA}$) across each channel of the $MoS_2$ membrane. All the conductances across $MoS_2$ membrane were obtained for a fixed Fermi energy value corresponding to a carrier concentration of $10^{12}/cm^2$.

Referring now to FIG. 7, this depicts an illustrative embodiment of a method 700 in accordance with various aspects described herein. As seen in this FIG. 7, step 702 comprises electronic sensing of an electrical characteristic associated with a translocation of a test DNA through a pore, wherein a feature of the test DNA comprises an epigenetic biomarker, the test DNA itself forming a conformational superstructure, or any combination thereof, and wherein the electronic sensing is performed by an electric current along the membrane that results in a sensed electrical characteristic. Next, step 704 comprises comparing the sensed electrical characteristic with a plurality of reference electrical characteristics, wherein each of the plurality of reference electrical characteristics is associated with a respective one of a plurality of reference features, and wherein the comparing results in a comparison result. Next, step 706 comprises determining, based upon the comparison result, with which of the plurality of reference features the feature of the test DNA corresponds. In various examples, the electronic sensing can be performed by an electric current along the membrane, the electronic sensing can be performed in accordance with an electric current along the membrane, or any combination thereof.

While for purposes of simplicity of explanation, the respective processes are shown and described as a series of blocks in FIG. 7, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 8:
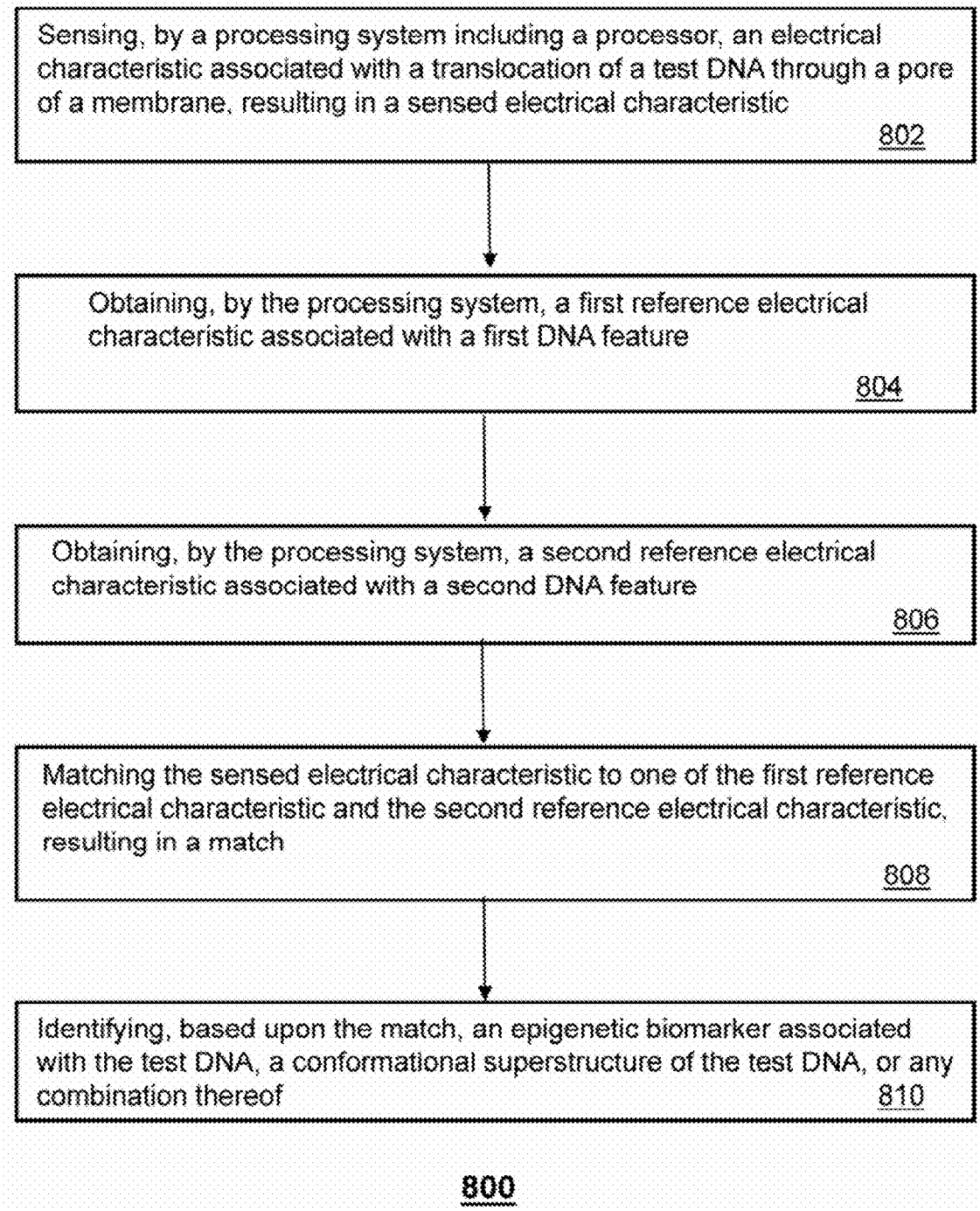
FIG. 8 depicts an illustrative method according to an embodiment.

Referring now to FIG. 8, this depicts an illustrative embodiment of a method 800 in accordance with various aspects described herein. As seen in this FIG. 8, step 802 comprises electronic sensing, by a processing system including a processor, of an electrical characteristic associated with a translocation of a test DNA through a pore of a membrane, the electronic sensing being performed by an electric current along the membrane that results in a sensed electrical characteristic. Next, step 804 comprises obtaining, by the processing system, a first reference electrical characteristic associated with a first DNA feature. Next, step 806 comprises obtaining, by the processing system, a second reference electrical characteristic associated with a second DNA feature. Next, step 808 comprises matching the sensed electrical characteristic to one of the first reference electrical characteristic and the second reference electrical characteristic, resulting in a match. Next, step 810 comprises identifying, based upon the match, an epigenetic biomarker associated with the test DNA, a conformational superstructure of the test DNA, or any combination thereof. In various examples, the electronic sensing can be performed by an electric current along the membrane, the electronic sensing can be performed in accordance with an electric current along the membrane, or any combination thereof.

While for purposes of simplicity of explanation, the respective processes are shown and described as a series of blocks in FIG. 8, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 9:
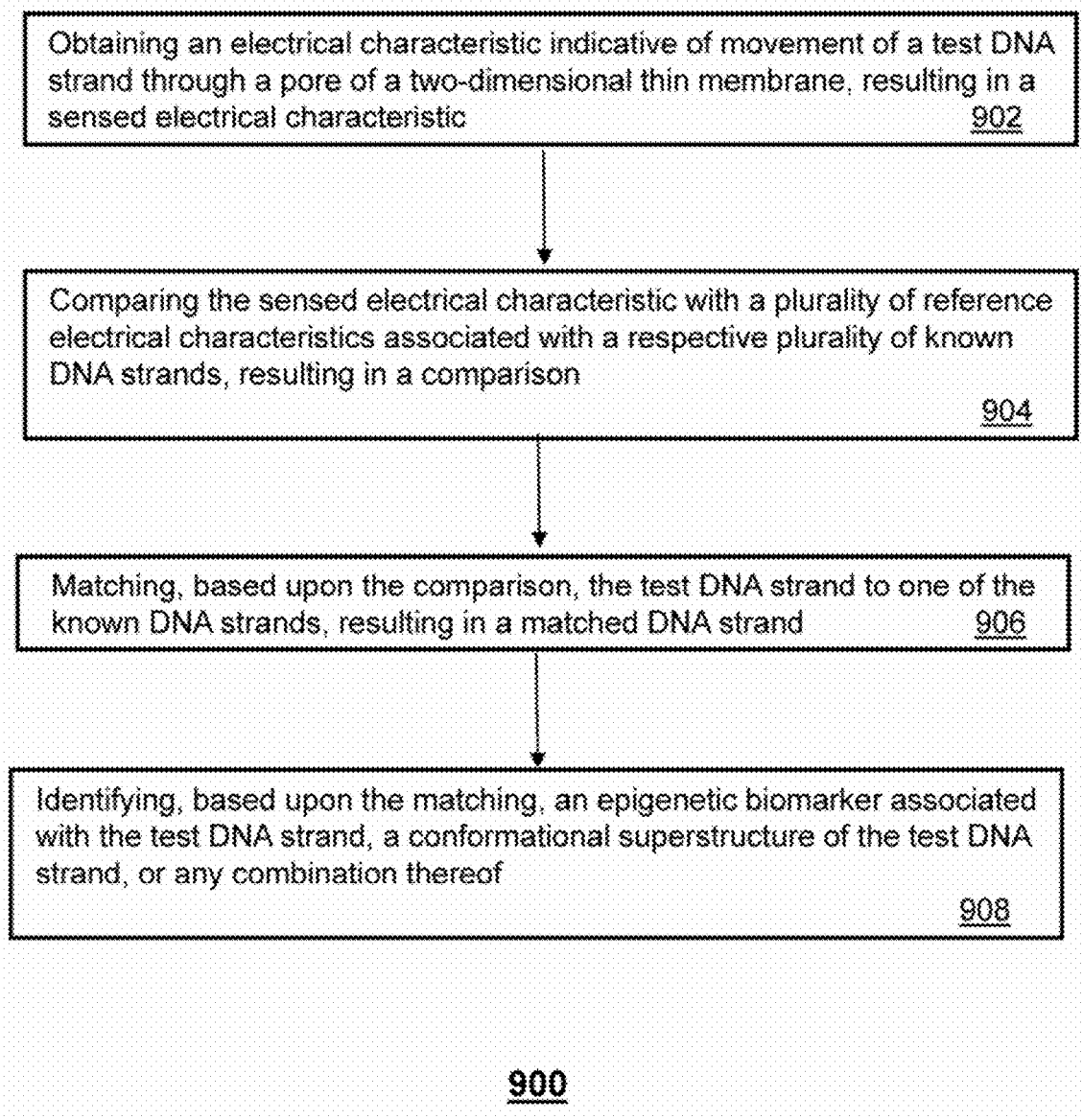
FIG. 9 depicts an illustrative method according to an embodiment.

Referring now to FIG. 9, this depicts an illustrative embodiment of a method 900 in accordance with various aspects described herein. As seen in this FIG. 9, step 902 comprises obtaining an electrical characteristic indicative of movement of a test DNA strand through a pore of a two-dimensional thin membrane, the electrical characteristic being obtained via electronic sensing performed by an electric current along the two-dimensional thin membrane that results in a sensed electrical characteristic. Next, step 904 comprises comparing the sensed electrical characteristic with a plurality of reference electrical characteristics associated with a respective plurality of known DNA strands, resulting in a comparison. Next, step 906 comprises matching, based upon the comparison, the test DNA strand to one of the known DNA strands, resulting in a matched DNA strand. Next, step 908 comprises identifying, based upon the matching, an epigenetic biomarker associated with the test DNA strand, a conformational superstructure of the test DNA strand, or any combination thereof. In various examples, the electronic sensing can be performed by an electric current along the membrane, the electronic sensing can be performed in accordance with an electric current along the membrane, or any combination thereof.

While for purposes of simplicity of explanation, the respective processes are shown and described as a series of blocks in FIG. 9, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

As described herein, various embodiments provide machine learning for enhanced nanopore bio-detection.

As described herein, DNA methylation is one of the most common epigenetic modifications in the eukaryotic genome, occurring primarily through the addition of methyl groups at the 5th-carbon of a cytosine ring. Methylation plays a crucial role in the expression of genes in mammalian cells and therefore is related to cell development, aging and progress of diseases such as cancer. In vertebrates, methylation typically occurs in DNA sequences with a relatively high content of CpG dinucleotides (namely, 5'-CG-3'), known as CpG islands. In cancerous cells, many of the CpG islands are observed to be methylated, while normal somatic cells are free of methylation. For this reason, DNA methylation holds the potential to serve as an effective biomarker that can be used in risk assessment and early diagnosis of methylation-relevant diseases such as cancer. It is therefore of crucial importance to detect and precisely map methylation patterns in the human epigenome.

As described herein, various embodiments can provide a low-cost, quick and reliable method to detect methylation on DNA. In various embodiments, the use of very thin membranes containing a pore with nanoscale feature sizes, through which DNA molecules are threaded to detect gene modifications can offer many advantages over conventional bio-chemical processes. Various embodiments can provide for the integration of solid state multi-layer nanopore membranes within a multi-functional electronic device to increase its detection sensitivity. Among the advantages of the solid state nanopore is its compatibility with semiconductor nano-electronics that favors the fabrication of compact devices, and opens the door to personalized medicine with revolutionary consequences for public health. Various embodiments can provide a methodology that combines electronic simulation based on device physics with advanced statistical signal processing to characterize the information-theoretic resolution limit of solid state nanopore sensing. Various embodiments can facilitate algorithms that approach these fundamental limits. These algorithms provide guidelines to improve the signal-to-noise ratio of the biomolecule-detecting membranes. As a study-case scenario, described herein is an assessment and achievement of the resolution limits for a nanopore device to detect methylated binding domain proteins on DNA. Identification of these proteins is critical, as their interactions with DNA have roles in breast, lung, and other kinds of cancers.

Various embodiments can provide for low-cost and fast DNA sequencing methods that can be used to facilitate personalized medicine, given its role in sequence-dependent diagnosis and treatment of diseases. Certain conventional technologies for methylation detection typically utilize large and expensive machines, relying on a dated method involving bi-sulphite genome sequencing. Nanopores, on the other hand, have great potential as next-generation sequencing devices, disrupting currently widespread technologies by offering improved accuracy at reduced sizes and costs for sequencing DNA along with multiple simultaneous modalities of electronically sensing DNA. Various embodiments can use solid state nanopores for epigenetic applications.

Various embodiments can facilitate a reduction in the cost of personalized medicine, enabling people to receive treatment suited to their individual DNA sequence.

Various embodiments can improve upon the typical low signal-to-noise ratio some solid state nanopores provide, thus easing detection of the DNA sequence or epigenetic DNA features. In various examples, robust identification algorithms are designed for solid state nanopores.

Figure 10:
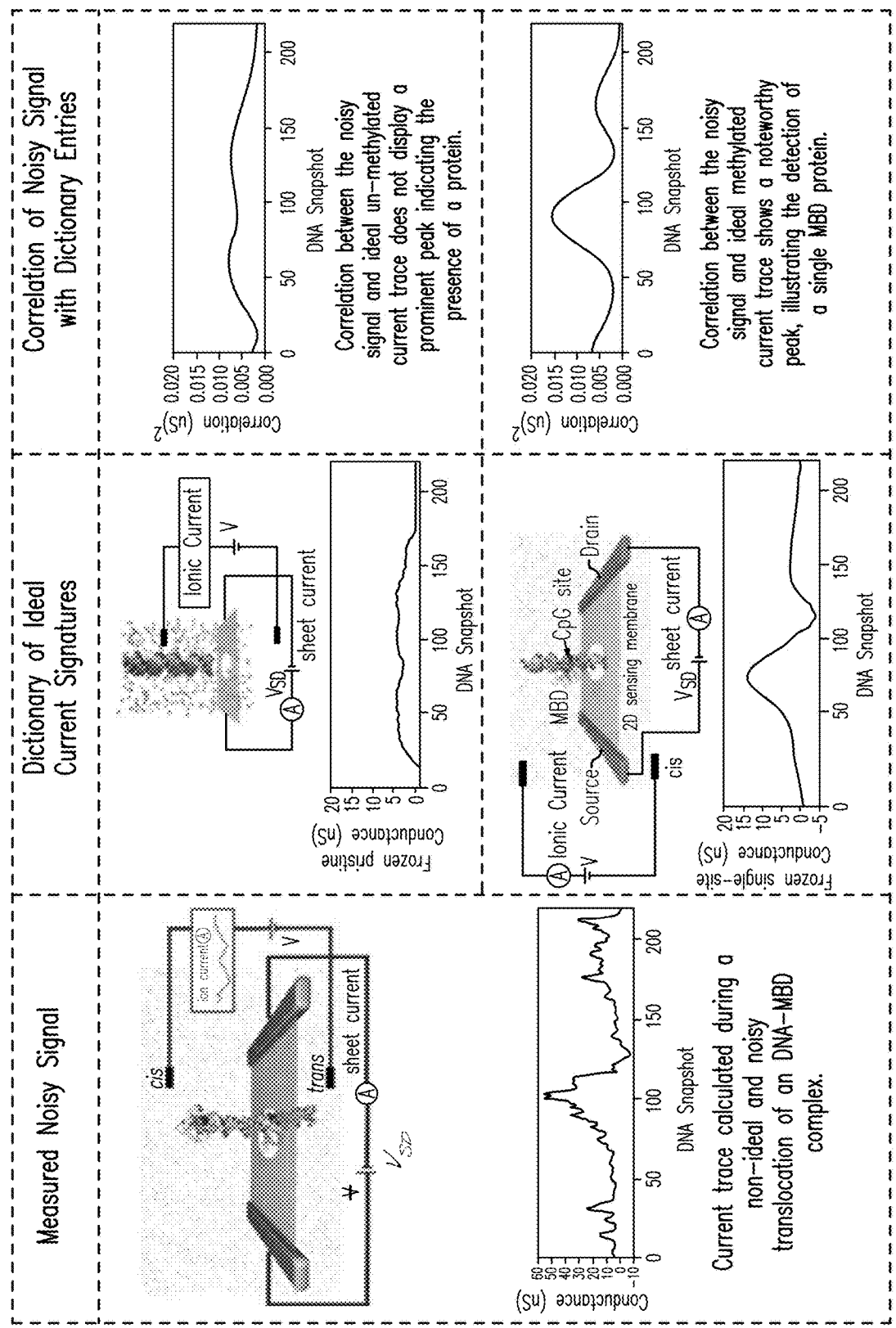
FIG. 10 depicts a set of simulations according to an embodiment. First computed is the electronic current due to the translocation of frozen unmethylated DNA and a frozen MBD1-DNA complex through a 5 nm molybdenum di-sulphide (MoS2) nanopore. The current signatures obtained for the frozen or "ideal" translocations are influenced only by the charge distribution along the biomolecular complexes and not by the noise introduced due to fluctuations. The current traces due to the frozen translocations are tabulated as the dictionary of ideal current signatures (shown in the middle column). As described herein, this dictionary can be extended to include (for example) the signatures due to other methyl-CpG binding domain proteins such as MBD2, MeCP2 etc. When a noisy current trace for the non-ideal translocation of a DNA-MBD complex containing only one MBD1 protein (as shown in the leftmost column (wherein $V_{SD}$ is the voltage shown between the Source on the left-hand side and the Drain on the right-hand side)) is correlated with each of the entries in the dictionary, observed is a peak when correlated with the entry corresponding to the frozen DNA-MBD current trace (see the rightmost column, bottom row) but not so when correlated with that of the pristine un-methylated current trace (see rightmost column, top row), demonstrating the validity of the approach.

In order to detect and map epigenetic features in DNA such as methylation patterns, various embodiments can utilize transverse sheet current in solid state nanopores with molybdenum di-sulphide ($MoS_2$) as the sensing membrane (see, e.g., FIG. 10). As demonstrated previously, transverse current offers a higher detection resolution than traditional sensing of DNA via ionic currents (see References 14A,1C). In various examples, a methodology of improving the signal-to-noise ratio is not limited to just transverse sheet current measurements in solid state nanopores but can also (or alternatively) be incorporated in the nanopore sequencing protocols which utilize ionic current signatures to potentially identify bases and methylation patterns. As described herein, as an example, is detection of the presence of a methyl-CpG binding domain protein attached to a CpG site in a ds-DNA. While a wide range of MBD proteins can be utilized for this purpose, employed (in this example) is the MBD1 protein as a biomarker for the methylation site along the DNA. Polymorphisms in the MBD1 protein have been shown to be significantly associated with lung cancer risk (see Reference 16A).

Some prior work (various features of which can be utilized by one or more embodiments) relates to a multi-functional electronic device made of solid state multi-layer nanopore membranes to increase bio-detection sensitivity (see References 2C, 3C). Such devices can offer advantages over certain conventional bio-chemical techniques (the advantages can include, for instance, compatibility with semiconductor nano-electronics that favors compact devices, and enables personalized medicine with revolutionary consequences for public health). However, many conventional efforts to detect, identify and map the DNA methylation patterns using solid state nanopores have been unsuccessful because the conformational stochastic fluctuations of DNA in electrolytic solution inside the pore introduces significant noise added to the measured signal. Further, some prior work (various features of which can be utilized by one or more embodiments) proposed a scenario to improve the signal-to-noise ratio in sequencing DNA with nanopore technology by stretching the bio-molecule (see Reference 12A). Various embodiments described herein provide a methodology that will impose limit in the detection resolution of epigenetic factors. Various embodiments described herein can comprise algorithms that provide guidelines to improve the signal-to-noise ratio of the bio-detecting membranes.

A drawback of certain conventional mechanisms in sensing biomolecules using nanopores has been the low signal-to-noise ratio of the measured current signals. The main source of the noise is due to fluctuations of the DNA as it translocates through the pore. Various embodiments described herein can provide for building a dictionary of "noise-free" current signatures for various proteins attached to methylated sites along the DNA. The "noise-free" current signatures are calculated (in various examples) via simulations where ideal and frozen biomolecules are translocated through the nanopore and the resulting current is calculated at each time instant. This process can be repeated for each of the MBD proteins, each of which is indicative of a different cancer (see Reference 16A).

Once the dictionary of signals is built, the resulting noisy signal from (for example) a methylated DNA-MBD complex translocation can be correlated with each of the dictionary entries. The correlation yields a prominent peak when the noisy signal is correlated with the ideal current signature of the same protein. In all other cases, the correlation does not yield a significant peak. The height of the peak in the correlated signal can be used to determine the validity of a particular hypothesis test (e.g., using the likelihood ratio test). A sample test case of this procedure is shown in FIG. 10 where the noisy current trace during a MBD-DNA complex translocation with a single MBD protein is correlated with each of the dictionary entries corresponding to the ideal "non-noisy" current signatures of pristine un-methylated DNA and a MBD-DNA respectively. The hypothesis corresponding to the presence of a single MBD1 protein is confirmed via the presence of the correlated signal peak. An important aspect to note here is the uniform resampling of each signal to correspond to a given fixed length.

In various examples, generalization of the disclosed techniques can incorporate different noise models and modification to include ionic current signatures. The technique described above in connection with FIG. 10 utilizes a Gaussian noise model with a simple matched filter implementation. In other embodiments, this can be generalized to incorporate many other noise models such as jitter noise, 1/f noise, and others, whether non-parametric descriptions or parametric noise models. Such other embodiments can also be generalized to incorporate factors of inter-symbol interference, as well as the possibility of memory in the epigenetic sequence itself. The likelihood ratio test can be modified for each of the different noise models used. Such other embodiments can also be generalized to be incorporated in the context of ionic current signatures. In other examples, the ideal "non-noisy" signals (e.g., for each of the methyl-CpG binding domain proteins) can be obtained by performing experiments many times over to get the statistically averaged current signature and noise characteristics. In other examples, the same procedure can be employed to identify the type of methyl-CpG protein and number of proteins as well.

As described herein, various embodiments relate to classification of epigenetic biomarkers via use of atomically-thin nanopores.

In one example, an algorithm is capable of calculating the electrical signatures (e.g., current signatures) of proteins and comparing them to other signatures (e.g., current signatures) in order to identify what protein is present in/on a strand of DNA.

In one example, the integration of a sensor with signal processing architectures as described herein could facilitate a multipurpose technology for early disease detection.

As described herein, various embodiments can provide for using a matched filter algorithm, whereby particular epigenetic markers are classified. In one example, a sensor technology is provided that is capable of detecting and mapping region(s) of hyper-methylation(s) across the genome by utilizing genetic marker(s). In one example, a sensor technology is provided that is capable of detecting and mapping regions of hypo-methylation(s) across the genome by utilizing genetic marker(s). In one example, mechanisms are provided to not only detect presence of one or more proteins, but to identify the one or more proteins (e.g., determine the type of each of the one or more proteins). In one example, the disclosed mechanisms can provide for early disease diagnosis.

As described herein, various embodiments (e.g., algorithms, processing applications) relate to DNA sequencing.

Unlike certain conventional nanopore sequencers (which are typically unable to identify epigenetic markers attached to methylated sites owing to size discrepancy between DNA-marker and the nanopore), various embodiments described herein are able to identify such epigenetic markers attached to methylated sites. In various embodiments, the resolution of detection of labeled sites via electronic current is limited by sizes of the labeled proteins rather than the electronic measurement quality itself. In various embodiments, nanopore sequencing can be provided with lower error rates than certain conventional technologies.

As described herein, various embodiments can use unique known electronic signals of proteins, in order to sequence DNA in real time (e.g., via comparison to other signatures to determine what proteins are present at methylated sites). In one example, an unknown signature can be placed through a filter, and once correlations between test and dictionary signals have been computed, the protein whose current signature provides the maximum Q factor is inferred to be present.

As described herein, an algorithm is provided that is capable of identifying the particular type of protein that exists in/on the DNA strand.

As described herein, an algorithm is provided for identifying protein(s) at a methylation site in order to facilitate early disease detection.

As described herein are mechanisms for the classification of epigenetic biomarkers via use of atomically-thin nanopores. In one example, provided is a low cost, fast, reliable method to access, and decode the human genome and/or epigenomes.

As described herein, various embodiments can utilize solid state nanopores. In one specific example, use of a 2D solid state nanopore can offer high detection resolution.

Various embodiments can improve upon certain conventional techniques to detect, identify and map DNA methylation patterns using sold state nanopores. Such conventional techniques have typically been unsuccessful because of significant noise introduced in the measured signal (such as due to the conformational stochastic fluctuations of DNA inside a pore). Various embodiments can provide improvement via use of an integrated approach that combines electronic simulations based on device physics with statistical signal processing techniques to characterize the resolution limit of solid state nanopore sensing and facilitate application of algorithms for epigenetic marker classification.

Various embodiments can provide a sensor technology that is capable of detecting and mapping regions of hyper-methylation(s) and/or hypo-methylation(s) across the genome by utilizing one or more bulky biomarkers.

In various embodiments, bulky groups can be used to label methylated cytosines along dsDNA (various examples can use methyl-CpG binding domain (MGD-1) protein or methyl CpG binding protein 2 (MeCP2) to identify regions of hyper-methylation. Another example can identify regions (such as sequences) of hypo-methylation, via detection of unmethylated CpGs marked by γ-cyclodextrin (GCD).

In various embodiments, the detection setup can utilize a 2D material (e.g., graphene, $MoS_2$, or other transition metal dichalcogenide membrane) connected between a source electrode and a drain electrode, enabling electron flow through the membrane. In one example, the detection sensitivity of the membrane can be controlled via a gate electrode separated from the membrane by high k dielectric. In another example, the nanopore can be circularly shaped (e.g., 5 nm). In one example, this can be the smallest size DNA marker complex that can be translocated without hindrance. In one example, the setup (e.g., the membrane with the nanopore) can be immersed in water with an electrolyte (e.g., KCl).

In various embodiments, reference signals can be utilized. In one example, the reference signals can be obtained from frozen DNA current signatures. In this example, for each noise-free reference signal, the observed current from the DNA marker complexes will arise solely from the charge distribution across the proteins which are unique to the protein structures themselves. The set of noise-free reference signals can comprise a set of unique reference current signatures for epigenetic markers. In one example, once the reference set is built, it can be used to identify the type and/or number of proteins by a statistical signal processing algorithm (e.g. a bank of matched filters).

As described herein, various embodiments can provide a system for detecting methylation of DNA.

One process according to an embodiment can be as follows: (a) contact a nucleic acid sequence with a bulky group label of methylated cytosines (e.g., methyl-CpG binding domain (MGD-1), GCD, methyl CpG binding protein 2 (MeCP2); (b) run the DNA through a solid state nanopore placed in an aqueous solution comprising an electrolyte, the solid state nanopore comprising: a 2D membrane (e.g., graphene, MoS2, other transition metal dichalcogenide) having at least one circular pore (~5 nm) and a source electrode and a drain electrode for applying current across the membrane; (c) measure the signals as the DNA moves through the pore; (d) compare the measured signals to at least one noise-free reference sample comprising a known signature for epigenetic markers.

As described herein, various embodiments can provide for detecting and/or classifying and/or counting one or more proteins attached to DNA. In one example, multiple proteins can be detected and/or classified and/or counted simultaneously.

As described herein, various embodiments can provide machine learning for enhanced nanopore bio-detection. In one example, the machine learning can be used for detecting and/or classifying and/or counting one or more proteins.

As described herein, various embodiments can provide for detecting proteins without a priori looking for that specific protein.

As described herein, various embodiments can be realized with hardware circuitry to carry out operations (e.g., such as operations to perform feature matching between the current signal of the test DNA strand with the corresponding feature(s) of the matched DNA strand). Such hardware circuitry can enable faster detection and identification of the test DNA. In various examples, such circuitry can be realized by a specific arrangement of silicon transistors on chip and/or by using reconfigurable circuitry such as Field Programmable Gate Arrays.

Figure 11:
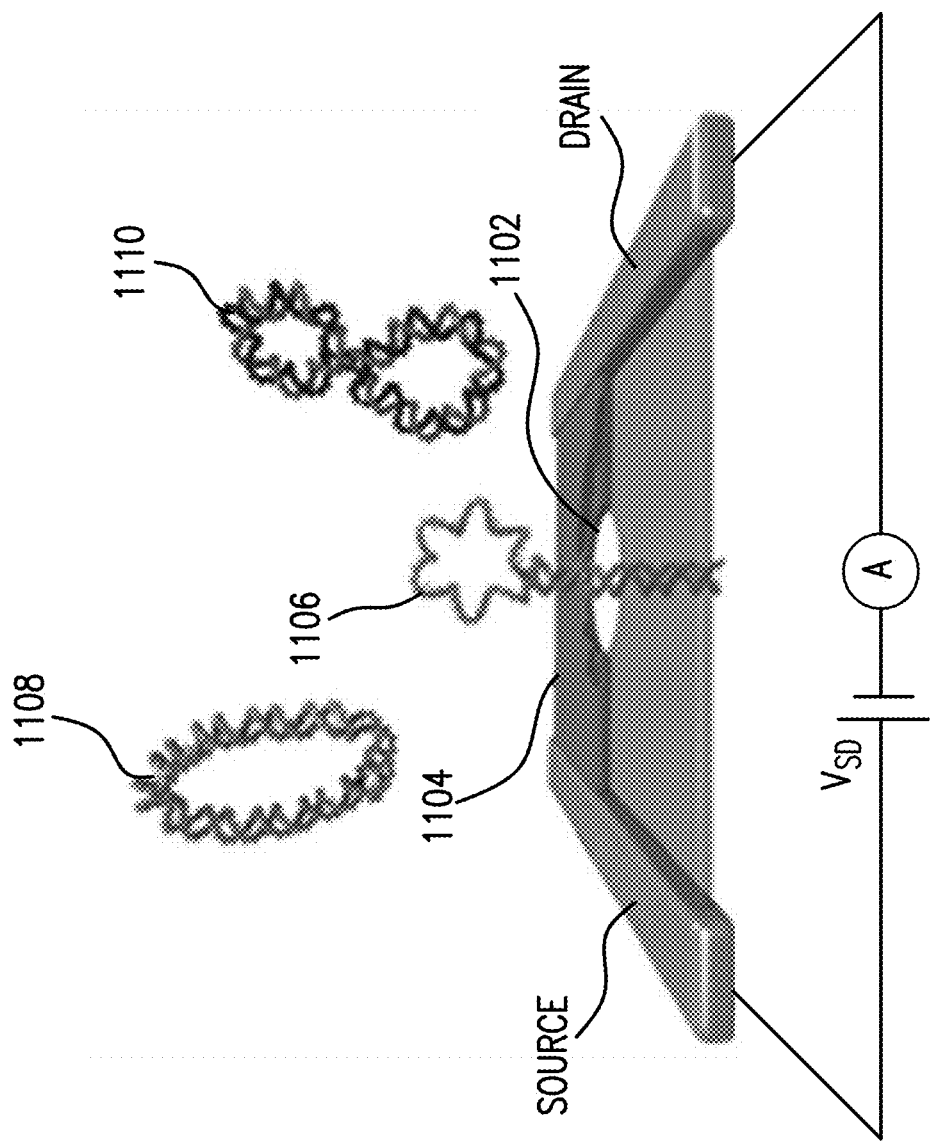
FIG. 11 depicts examples of various DNA superstructures that can be detected according to various embodiments.

Referring now to FIG. 11, this depicts examples of various DNA superstructures that can be detected according to various embodiments. More particularly, this FIG. 11 depicts a schematic illustration of three kinds of DNA superstructures that can be detected (according to algorithms and/or detectors of various embodiments) when the superstructures translocate through a nanopore 1102 in a two-dimensional membrane 1104. The DNA 1106 (shown in the pore) is called a "hairpin". The DNA 1108 (shown on the upper left) is called a "DNA loop". The DNA 1110 (shown on the upper right) is called a "twisted loop" (with a binding complex in the middle).

From the foregoing descriptions, it would be evident to an artisan with ordinary skill in the art that the aforementioned embodiments can be modified, reduced, or enhanced without departing from the scope and spirit of the claims described below. For example, any desired number and/or type of reference signatures can be utilized. Other suitable modifications can be applied to the subject disclosure. Accordingly, the reader is directed to the claims for a fuller understanding of the breadth and scope of the subject disclosure.

Figure 12:
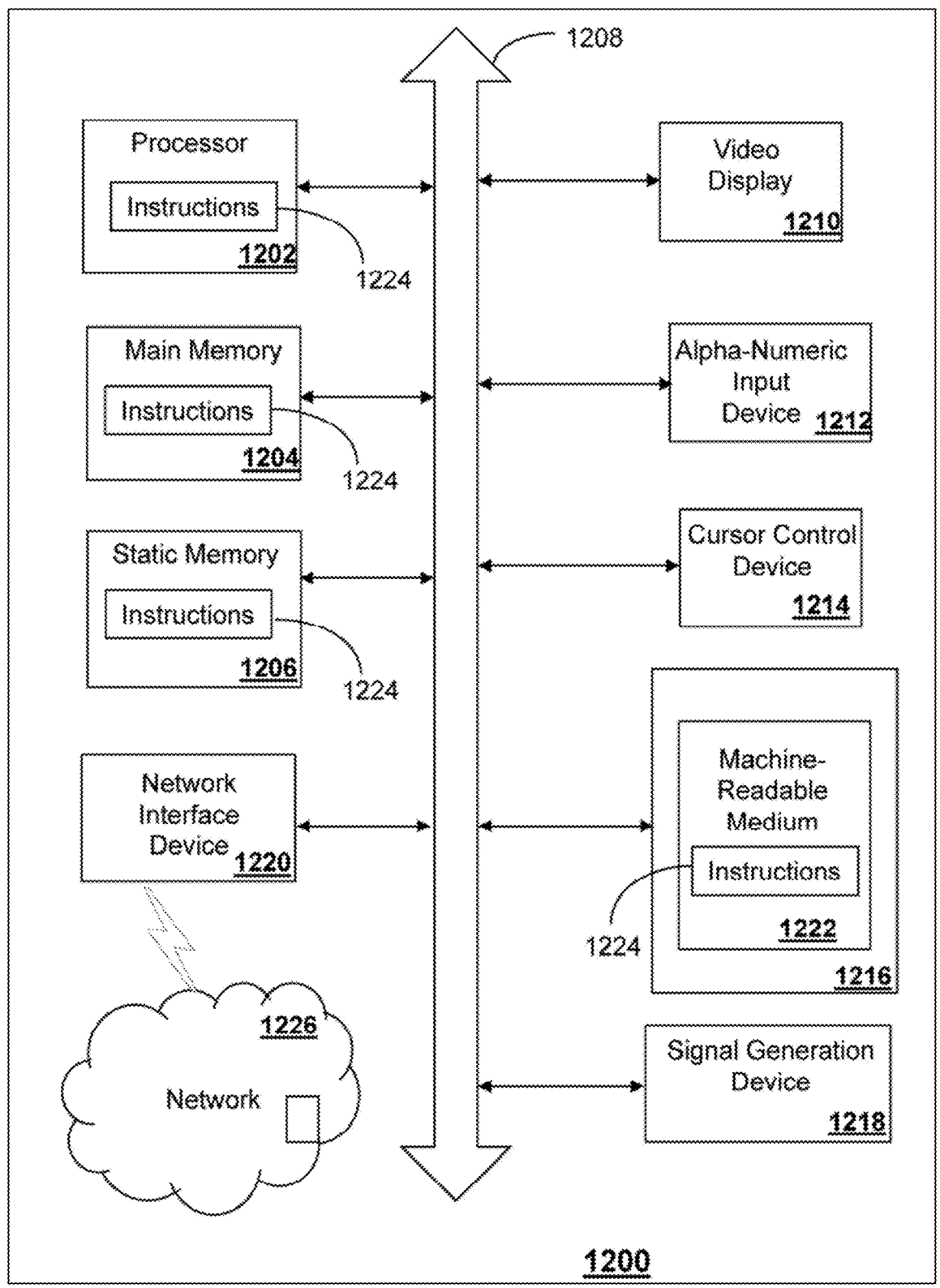
FIG. 12 depicts an illustrative diagrammatic representation of a machine in the form of a computer system within which a set of instructions, when executed, can cause the machine to perform any one or more of the methodologies disclosed herein.

FIG. 12 depicts an example diagrammatic representation of a machine in the form of a computer system 1200 within which a set of instructions, when executed, can cause the machine to perform any one or more of the methods discussed above. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1200 may include a processor 1202 (e.g., a central processing unit (CPU), a graphics processing unit (GPU, or both), a main memory 1204 and a static memory 1206, which communicate with each other via a bus 1208. The computer system 1200 may further include a video display unit 1210 (e.g., a liquid crystal display (LCD), a flat panel, or a solid state display. The computer system 1200 may include an input device 1212 (e.g., a keyboard), a cursor control device 1214 (e.g., a mouse), a disk drive unit 1216, a signal generation device 1218 (e.g., a speaker or remote control) and a network interface device 1220.

The disk drive unit 1216 may include a tangible computer-readable storage medium 1222 on which is stored one or more sets of instructions (e.g., software 1224) embodying any one or more of the methods or functions described herein, including those methods illustrated above. The instructions 1224 may also reside, completely or at least partially, within the main memory 1204, the static memory 1206, and/or within the processor 1202 during execution thereof by the computer system 1200. The main memory 1204 and the processor 1202 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 1222 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 1200.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

REFERENCES (1A) Bayley, H. Nanotechnology: holes with an edge. Nature 2010, 467, 164-165.
(2A) Ehrlich, M. DNA methylation in cancer: too much, but also too little. Oncogene 2002, 21, 5400-5413.
(3A) Kilianski, A.; Haas, J. L.; Corriveau, E. J.; Liem, A. T.; Willis, K. L.; Kadavy, D. R.; Rosenzweig, C. N.; Minot, S. S. Bacterial and viral identification and differentiation by amplicon sequencing on the MinION nanopore sequencer. GigaScience 2015, 4, 12.
(4A) Gracheva, M. E.; Xiong, A.; Aksimentiev, A.; Schulten, K.; Timp, G.; Leburton, J.-P. Simulation of the electric response of DNA translocation through a semiconductor nanopore capacitor. Nanotechnology 2006, 17, 622-633.
(5A) Gracheva, M. E.; Aksimentiev, A.; Leburton, J.-P. Electrical signatures of single-stranded DNA with single base mutations in a nanopore capacitor. Nanotechnology 2006, 17, 3160-3165.
(6A) Heerema, S. J.; Dekker, C. Graphene nanodevices for DNA sequencing. Nat. Nanotechnol. 2016, 11, 127-136.
(7A) Laszlo, A. H.; Derrington, I. M.; Brinkerhoff, H.; Langford, K. W.; Nova, I. C.; Samson, J. M.; Bartlett, J. J.; Pavlenok, M.; Gundlach, J. H. Detection and mapping of 5-methylcytosine and 5-hydroxymethylcytosine with nanopore MspA. Proc. Natl. Acad. Sci. U.S.A. 2013, 110, 18904-18909.
(8A) Shim, J.; Kim, Y.; Humphreys, G. I.; Nardulli, A. M.; Kosari, F.; Vasmatzis, G.; Taylor, W. R.; Ahlquist, D. A.; Myong, S.; Bashir, R. Nanopore-based assay for detection of methylation in doublestranded DNA fragments. ACS Nano 2015, 9, 290-300.
(9A) Jain, M.; Koren, S.; Miga, K. H.; Quick, J.; Rand, A. C.; Sasani, T. A.; Tyson, J. R.; Beggs, A. D.; Dilthey, A. T.; Fiddes, I. T.; et al. Nanopore sequencing and assembly of a human genome with ultralong reads. Nat. Biotechnol. 2018, 36, 338-345.
(10A) Garalde, D. R.; Snell, E. A.; Jachimowicz, D.; Sipos, B.; Lloyd, J. H.; Bruce, M.; Pantic, N.; Admassu, T.; James, P.; Warland, A.; et al. Highly parallel direct RNA sequencing on an array of nanopores. Nat. Methods 2018, 15, 201-206.
(11A) Girdhar, A.; Sathe, C.; Schulten, K.; Leburton, J.-P. Graphene quantum point contact transistor for DNA sensing. Proc. Natl. Acad. Sci. U.S.A. 2013, 110, 16748-16753.
(12A) Qiu, H.; Sarathy, A.; Leburton, J.-P.; Schulten, K. Intrinsic stepwise translocation of stretched ssDNA in graphene nanopores. Nano Lett. 2015, 15, 8322-8330.
(13A) Sarathy, A.; Qiu, H.; Leburton, J.-P. Graphene nanopores for electronic recognition of DNA methylation. J. Phys. Chem. B 2017, 121, 3757-3763.
(14A) Qiu, H.; Sarathy, A.; Schulten, K.; Leburton, J.-P. Detection and mapping of DNA methylation with 2D material nanopores. npj 2D Mater. Appl. 2017, 1, 3.
(15A) Gilboa, T.; Torfstein, C.; Juhasz, M.; Grunwald, A.; Ebenstein, Y.; Weinhold, E.; Meller, A. Single-Molecule DNA Methylation Quantification Using Electro-optical Sensing in Solid-State Nanopores. ACS Nano 2016, 10, 8861-8870.
(16A) Parry, L.; Clarke, A. R. The roles of the methyl-CpG binding proteins in cancer. Genes Cancer 2011, 2, 618-630.
(17A) Du, Q.; Luu, P.-L.; Stirzaker, C.; Clark, S. J. Methyl-CpGbinding domain proteins: readers of the epigenome. Epigenomics 2015, 7, 1051-1073.
(18A) Lopez-Serra, L.; Esteller, M. Proteins that bind methylated DNA and human cancer: reading the wrong words. Br. J. Cancer 2008, 98, 1881-1885.
(19A) Jang, J.-S.; Lee, S. J.; Choi, J. E.; Cha, S. I.; Lee, E. B.; Park, T. I.; Kim, C. H.; Lee, W. K.; Kam, S.; Choi, J.-Y.; et al. Methyl-CpG binding domain 1 gene polymorphisms and risk of primary lung cancer. Cancer Epidemiol. Prev. Biomarkers 2005, 14, 2474-2480.
(20A) North, D. O. An Analysis of the factors which determine signal/noise discrimination in pulsed-carrier systems. Proc. IEEE 1963, 51, 1016-1027.
(21A) Woodward, P. M. Probability and Information Theory, With Applications to Radar; McGraw-Hill: New York, 1953.
(22A) Turin, G. An introduction to matched filters. IRE Trans. Inf. Theory 1960, IT-6, 311-329.
(23A) Raillon, C.; Granjon, P.; Graf, M.; Steinbock, L.; Radenovic, A. Fast and automatic processing of multi-level events in nanopore translocation experiments. Nanoscale 2012, 4, 4916-4924.
(24A) Kotelnikov, V. A. The Theory of Optimum Noise Immunity; McGraw-Hill: New York, 1959.
(25A) Furth, P. M.; Andreou, A. G. A design framework for low power analog filter banks. IEEE Trans. Circuits Syst. I, Fundam. Theory Appl. 1995, 42, 966-971.
(26A) Parkin, W. M.; Drndić, M. Signal and Noise in FET-Nanopore Devices. ACS Sensors 2018, 3, 313-319.
(27A) Simpson, J. T.; Workman, R. E.; Zuzarte, P.; David, M.; Dursi, L.; Timp, W. Detecting DNA cytosine methylation using nanopore sequencing. Nat. Methods 2017, 14, 407-410.
(28A) Heerema, S. J.; Vicarelli, L.; Pud, S.; Schouten, R. N.; Zandbergen, H. W.; Dekker, C. Probing DNA translocations with inplane current signals in a graphene nanoribbon with a nanopore. ACS Nano 2018, 12, 2623-2633.
(29A) Athreya, N. B. M.; Sarathy, A.; Leburton, J.-P. Large Scale Parallel DNA Detection by Two-Dimensional Solid-State Multipore Systems. ACS Sensors 2018, 3, 1032-1039.
(1B) Phillips, J. C.; Braun, R.; Wang, W.; Gumbart, J.; Tajkhorshid, E.; Villa, E.; Chipot, C.; Skeel, R. D.; Kal, L.; Schulten, K. Scalable molecular dynamics with NAMD. Journal of Computational Chemistry 2005, 26, 1781{1802.
(2B) Humphrey, W.; Dalke, A.; Schulten, K. VMD: visual molecular dynamics. J. Mol. Graphics 1996, 14, 33{38.
(3B) Ohki, I.; Shimotake, N.; Fujita, N.; Jee, J.-G.; Ikegami, T.; Nakao, M.; Shirakawa, M. Solution Structure of the Methyl-CpG Binding Domain of Human MBD1 in Complex with Methylated DNA. Cell 2001, 105, 487 { 497.
(4B) Ho, K. L.; McNae, I. W.; Schmiedeberg, L.; Klose, R. J.; Bird, A. P.; Walkinshaw, M. D. MeCP2 Binding to DNA Depends upon Hydration at Methyl-CpG. Molecular Cell 2008, 29, 525 { 531.
(5B) Saenger, W.; Jacob, J.; Gessler, K.; Steiner, T.; Ho mann, D.; Sanbe, H.; Koizumi, K.; Smith, S. M.; Takaha, T. Structures of the Common Cyclodextrins and Their Larger Analogues—Beyond the Doughnut. Chemical Reviews 1998, 98, 1787{1802.
(6B) MacKerell, A. D.; Bashford, D.; Bellott, M.; Dunbrack, R. L.; Evanseck, J. D.; Field, M. J.; Fischer, S.; Gao, J.; Guo, H.; Ha, S. et al. All-Atom Empirical Potential for Molecular Modeling and Dynamics Studies of Proteins. The Journal of Physical Chemistry B 1998, 102, 3586{3616.
(7B) van Dijk, M.; Bonvin, A. M. J. J. 3D-DART: a DNA structure modelling server. Nucleic Acids Research 2009, 37, W235{W239.
(8B) Foloppe, N.; MacKerell, A. D., Jr. All-atom empirical force field for nucleic acids: I. Parameter optimization based on small molecule and condensed phase macromolecular target data. Journal of Computational Chemistry 2000, 21, 86{104.
(9B) Stewart, J. A.; Spearot, D. Atomistic simulations of nanoindentation on the basal plane of crystalline molybdenum disul de (MoS2). Modelling and Simulation in Materials Science and Engineering 2013, 21, DOI: 10.1088/0965-0393/21/4/045003.
(10B) Jorgensen, W. L.; Chandrasekhar, J.; Madura, J. D.; Impey, R. W.; Klein, M. L. Comparison of simple potential functions for simulating liquid water. J. Chem. Phys. 1983, 79, 926{935.
(11B) Essmann, U.; Perera, L.; Berkowitz, M. L.; Darden, T.; Lee, H.; Pedersen, L. G. A smooth particle mesh Ewald method. J. Chem. Phys. 1995, 103, 8577{8593.
(12B) Feller, S. E.; Zhang, Y.; Pastor, R. W.; Brooks, B. R. Constant pressure molecular dynamics simulation: the Langevin piston method. J. Chem. Phys. 1995, 103, 4613{4621.
(13B) Sathe, C.; Zou, X.; Leburton, J.-P.; Schulten, K. Computational investigation of DNA detection using graphene nanopores. ACS Nano 2011, 5, 8842{8851.
(14B) Gracheva, M. E.; Leburton, J.-P. Electrolytic charge inversion at the liquid{ solid interface in a nanopore in a doped semiconductor membrane. Nanotechnology 18, DOI:10.1088/0957-4484/18/14/145704.
(15B) Gracheva, M. E.; Vidal, J.; Leburton, J.-P. p-n Semiconductor Membrane for Electrically Tunable Ion Current Recti cation and Filtering. Nano letters 2007, 7, 1717{1722.
(1C) Aditya Sarathy and Jean-Pierre Leburton, "Transport Model for Electronic Conductance in MoS2 with Nanopores" Appl. Phys. Letters. 108, 053701 (2016).
(2C) U.S. Pat. No. 8,192,600 (issued on Jun. 5, 2012 and entitled "Solid State Device") and U.S. Pat. No. 8,702,929 (issued on Apr. 22, 2014) and entitled "Solid State Device").
(3C) U.S. patent application Ser. No. 14/781,106, entitled "Method And Apparatus Analyzing A Target Material", and published as U.S. Patent Application Publication No. 2016/0054260.

What is claimed is:

1. An apparatus comprising:
a database comprising a dictionary of reference signals, each of the reference signals corresponding to one of methyl-CpG binding domain (MBD-1) protein, methyl CpG binding protein 2 (MeCP2), or γcyclodextrin (GCD);
a membrane, wherein the membrane has a first side and a second side, wherein the membrane has a pore disposed therein, wherein the pore extends through the membrane from the first side of the membrane to the second side of the membrane;
a processing system including a processor; and
a memory that stores executable instructions that, when executed by the processing system, facilitate performance of operations, the operations comprising:
electronic sensing of an electrical characteristic associated with a translocation of a test DNA through the pore, wherein a feature of the test DNA comprises an epigenetic biomarker, and wherein the electronic sensing is performed by an electric current along the membrane that results in a sensed electrical characteristic;
comparing the sensed electrical characteristic with each of the reference signals of the dictionary, wherein the comparing results in a comparison result; and
determining, based upon the comparison result, with which of the reference signals of the dictionary the sensed electrical characteristic corresponds, resulting in a corresponding reference signal, wherein the determining comprises determining that at least a first correlation peak between the corresponding reference signal and the sensed electrical characteristic is above a threshold and that at least a second correlation peak between the corresponding reference signal and the sensed electrical characteristic is above the threshold.

2. The apparatus of claim 1, wherein the sensed electrical characteristic comprises a sensed current, a sensed voltage, or a combination thereof.

3. The apparatus of claim 2, wherein each of the reference signals of the dictionary comprise a reference current, a reference voltage, or a combination thereof.

4. The apparatus of claim 3, wherein the comparing comprises:
comparing the sensed current to each of the reference currents; or
comparing the sensed voltage to each of the reference voltages; or
comparing the sensed combination to each of the reference combinations.

5. The apparatus of claim 1, wherein the first side of the membrane is a top surface, and wherein the second side of the membrane is a bottom surface.

6. The apparatus of claim 1, wherein the determining comprises determining with which of the reference signals of the dictionary the sensed electrical characteristic corresponds most closely, relative to each other ones of the reference signals of the dictionary.

7. The apparatus of claim 1, wherein:
the translocation is movement of part of the test DNA through the pore.

8. The apparatus of claim 1, wherein:
each of the MBD-1, the MeCP2, the GCP and any other arbitrary epigenetic biomarker is attached to a respective double stranded DNA.

9. The apparatus of claim 1, wherein:
the operations further comprise identifying, based upon with which of the reference signals of the dictionary the sensed electrical characteristic corresponds, a region on the test DNA of either hypo-methylation or hyper-methylation.

10. The apparatus of claim 1, wherein each of the sensed electrical characteristic and the reference signals of the dictionary varies over time.

11. An apparatus comprising:
a database comprising a dictionary of reference signals, each of the reference signals corresponding to one of methyl-CpG binding domain (MBD-1) protein, methyl CpG binding protein 2 (MeCP2), or γcyclodextrin (GCD);
a membrane, wherein the membrane has a first side and a second side, wherein the first side of the membrane is a top surface, wherein the second side of the membrane is a bottom surface, wherein the membrane has a pore disposed therein, wherein the pore extends through the membrane from the top surface of the membrane to the bottom surface of the membrane;
a processing system including a processor; and
a memory that stores executable instructions that, when executed by the processing system, facilitate performance of operations, the operations comprising:
electronic sensing of an electrical characteristic associated with a translocation of a test DNA through the pore, wherein a feature of the test DNA comprises an epigenetic biomarker, wherein the electronic sensing is performed by an electric current along the membrane that results in a sensed electrical characteristic, and wherein the sensed electrical characteristic comprises a sensed current, a sensed voltage, or a sensed combination thereof;
comparing the sensed electrical characteristic with each of the reference signals of the dictionary, wherein each of the reference signals of the dictionary comprise a reference current, a reference voltage, or a reference combination thereof, wherein each of the sensed electrical characteristic and each of the reference signals of the dictionary varies over time, and wherein the comparing results in a comparison result; and
determining, based upon the comparison result, with which of the reference signals of the dictionary the sensed electrical characteristic corresponds, resulting in a corresponding reference signal, wherein the determining comprises determining that at least a first correlation peak between the corresponding reference signal and the sensed electrical characteristic is above a threshold and that at least a second correlation peak between the corresponding reference signal and the sensed electrical characteristic is above the threshold.

12. The apparatus of claim 11, wherein the comparing comprises:
comparing the sensed current to each of the reference currents; or
comparing the sensed voltage to each of the reference voltages; or
comparing the sensed combination to each of the reference combinations.

13. The apparatus of claim 11, wherein the determining comprises determining with which of the reference signals of the dictionary the electrical characteristic corresponds most closely, relative to each other ones of the reference signals of the dictionary.

14. The apparatus of claim 11, wherein:
the operations further comprise identifying, based upon with which of the reference signals of the dictionary the sensed electrical characteristic corresponds, a region on the test DNA of either hypo-methylation or hyper-methylation.

15. An apparatus comprising:
a database comprising a plurality of reference signals, each of the plurality of reference signals corresponding to one of methyl-CpG binding domain (MBD-1) protein, methyl CpG binding protein 2 (MeCP2), or γcyclodextrin (GCD);
a membrane, wherein the membrane has a first side and a second side, wherein the membrane has a pore disposed therein, wherein the pore extends through the membrane from the first side of the membrane to the second side of the membrane;
a processing system including a processor; and
a memory that stores executable instructions that, when executed by the processing system, facilitate performance of operations, the operations comprising:
electronic sensing of an electrical characteristic associated with a translocation of a test DNA through the pore, wherein the translocation is movement of part of the test DNA through the pore, wherein a feature of the test DNA comprises an epigenetic biomarker, and wherein the electronic sensing is performed by an electric current along the membrane that results in a sensed electrical characteristic;
comparing the sensed electrical characteristic each of the plurality of reference signals, and wherein the comparing results in a comparison result; and
determining, based upon the comparison result, with which of the plurality of reference signals the sensed electrical characteristic corresponds, resulting in a corresponding reference signal, wherein the determining comprises determining that at least a first correlation peak between the corresponding reference signal and the sensed electrical characteristic is above a threshold and that at least a second correlation peak between the corresponding reference signal and the sensed electrical characteristic is above the threshold, and wherein the determining comprises determining with which of the plurality of reference signals the sensed electrical characteristic corresponds most closely, relative to each other ones of the plurality of reference signals.

16. The apparatus of claim 15, wherein the sensed electrical characteristic comprises a sensed current, a sensed voltage, or a combination thereof.

17. The apparatus of claim 16, wherein each of the plurality of reference signals comprise a reference current, a reference voltage, or a combination thereof.

18. The apparatus of claim 17, wherein the comparing comprises:
comparing the sensed current to each of the reference currents; or
comparing the sensed voltage to each of the reference voltages; or
comparing the sensed combination to each of the reference combinations.

19. The apparatus of claim 15, wherein each of the sensed electrical characteristic and the plurality of reference signals varies over time, wherein the first side of the membrane is a top surface, and wherein the second side of the membrane is a bottom surface.

20. The apparatus of claim 15, wherein:
the operations further comprise identifying, based upon with which of the plurality of reference signals the sensed electrical characteristic corresponds, a region on the test DNA of either hypo-methylation or hyper-methylation.

* * * * *